US012799528B2

(12) United States Patent
Pan et al.

(10) Patent No.: US 12,799,528 B2
(45) Date of Patent: Nov. 17, 2026

(54) METHOD FOR MEDIUM-THROUGHPUT MULTI-SINGLE-CELL REPRESENTATIVE DNA METHYLATION LIBRARY CONSTRUCTION AND SEQUENCING

(71) Applicant: Shenzhen Huateng Cloud Computing Co., Ltd, Shenzhen (CN)

(72) Inventors: Xinghua Pan, Guangzhou (CN); Liyao Mai, Guangzhou (CN); Zhiwei Lian, Guangzhou (CN)

(73) Assignee: Shenzhen Huateng Cloud Computing Co., Ltd, Shenzhen (CN)

( * ) Notice: Subject to any disclaimer, the term of this patent is extended or adjusted under 35 U.S.C. 154(b) by 481 days.

(21) Appl. No.: 18/372,695

(22) Filed: Sep. 25, 2023

(65) Prior Publication Data

US 2024/0132949 A1 Apr. 25, 2024
US 2024/0229125 A9 Jul. 11, 2024

Related U.S. Application Data

(63) Continuation-in-part of application No. PCT/CN2022/073322, filed on Jan. 21, 2022.

(30) Foreign Application Priority Data

Mar. 25, 2021 (CN) ......................... 202110336815.7

(51) Int. Cl.

| | |
|---|---|
| ***C12Q 1/6869*** | (2018.01) |
| ***C12Q 1/44*** | (2006.01) |
| ***C12Q 1/48*** | (2006.01) |
| ***C12Q 1/6806*** | (2018.01) |
| ***C12Q 1/686*** | (2018.01) |

(52) U.S. Cl.

CPC ............. *C12Q 1/6869* (2013.01); *C12Q 1/44* (2013.01); *C12Q 1/485* (2013.01); *C12Q 1/6806* (2013.01); *C12Q 1/686* (2013.01); *C12Q 2600/154* (2013.01); *C12Y 207/07* (2013.01)

(58) Field of Classification Search

CPC ........ C12Q 1/6869; C12Q 1/44; C12Q 1/485; C12Q 1/6806; C12Q 1/686; C12Q 2600/154; C12Q 1/6858; C12Q 1/6876; C12Y 207/07; C12N 15/11; C40B 50/06
See application file for complete search history.

(56) References Cited

U.S. PATENT DOCUMENTS 9,745,614 B2 * 8/2017 Schroeder ............ C12Q 1/6806
2004/0219580 A1 11/2004 Dunn et al.
2020/0248175 A1 8/2020 van Galen et al.

FOREIGN PATENT DOCUMENTS

CN 104694635 A 6/2015
CN 105002567 A 10/2015
CN 105200530 A 12/2015
CN 108179174 A 6/2018

OTHER PUBLICATIONS

Boyle et al., Genome Biology, 13:R92, 1-10, (Year: 2012).*
International Search Report of PCT Patent Application No. PCT/CN2022/073322 issued on Apr. 20, 2022.
Lin Han et al., Bisulfite-independent analysis of CpG island methylation enables genome-scale stratification of single cells, Nucleic Acids Research, Jan. 25, 2017, pp. 1-13, vol. 45, No. 10.
Liyao Mai et al., Shortcut barcoding and early pooling for scalable multiplex single-cell reduced-representation CpG methylation sequencing at single nucleotide resolution, Nucleic Acids Research, 2023, pp. 1-14.

* cited by examiner

*Primary Examiner* — Cynthia B Wilder

(57) ABSTRACT

Disclosed is a set of adhesive adapters containing sample barcodes for specifically tagging different samples. Further disclosed is a method for simultaneously detecting CpG methylation in a high number of samples, which is multi-sample reduced-representation bisulfite sequencing (msRRBS); and an alternative method thereof, which is multi-sample reduced-representation APOBEC sequencing (msRRAS). The adapters are used to specifically tag the plurality of samples, including all DNA fragments of the plurality of samples; then the plurality of samples are pooled to allow a single-tube reaction of the plurality of samples; and then the subsequent conversion, sequencing library construction and sequencing, distribution and decoding of readings of each sample, and downstream analysis are conducted. The library construction technology of the present application has advantages such as high efficiency, low cost, and stable and convenient operations.

19 Claims, 15 Drawing Sheets

Specification includes a Sequence Listing.

（SEQ ID NO：1，Oligo 2）

5′-AAGTAGGTATC$_m$C$_m$GTGAGTGGTGAAGAAT-3′

3′-/3Amino/ACCACTTCTTAGC-5′

（SEQ ID NO：2，Oligo 1）

FIG. 4

SEQUENCE LISTING

```
Sequence total quantity: 16
SEQ ID NO: 1            moltype = DNA  length = 28
FEATURE                 Location/Qualifiers
source                  1..28
                        mol_type = other DNA
                        organism = synthetic construct
misc_feature            1..28
                        note = synthetic
SEQUENCE: 1
aagtaggtat ccgtgagtgg tgaagaat                                  28

SEQ ID NO: 2            moltype = DNA  length = 13
FEATURE                 Location/Qualifiers
source                  1..13
                        mol_type = other DNA
                        organism = synthetic construct
misc_feature            1..13
                        note = synthetic
SEQUENCE: 2
cgattcttca cca                                                  13

SEQ ID NO: 3            moltype = DNA  length = 22
FEATURE                 Location/Qualifiers
source                  1..22
                        mol_type = other DNA
                        organism = synthetic construct
```

-continued

```
misc_feature           1..22
                       note = synthetic
SEQUENCE: 3
aagtaggtat ccgtgagtgg tg                                              22

SEQ ID NO: 4           moltype =   length =
SEQUENCE: 4
000

SEQ ID NO: 5           moltype = DNA  length = 28
FEATURE                Location/Qualifiers
source                 1..28
                       mol_type = other DNA
                       organism = synthetic construct
misc_feature           1..28
                       note = synthetic
SEQUENCE: 5
aagtaggtat ccgtgagtgg tgtaagta                                        28

SEQ ID NO: 6           moltype = DNA  length = 13
FEATURE                Location/Qualifiers
source                 1..13
                       mol_type = other DNA
                       organism = synthetic construct
misc_feature           1..13
                       note = synthetic
SEQUENCE: 6
cgtacttaca cca                                                        13

SEQ ID NO: 7           moltype = DNA  length = 28
FEATURE                Location/Qualifiers
source                 1..28
                       mol_type = other DNA
                       organism = synthetic construct
misc_feature           1..28
                       note = synthetic
SEQUENCE: 7
aagtaggtat ccgtgagtgg tgagttat                                        28

SEQ ID NO: 8           moltype = DNA  length = 13
FEATURE                Location/Qualifiers
source                 1..13
                       mol_type = other DNA
                       organism = synthetic construct
misc_feature           1..13
                       note = synthetic
SEQUENCE: 8
cgataactca cca                                                        13

SEQ ID NO: 9           moltype = DNA  length = 28
FEATURE                Location/Qualifiers
source                 1..28
                       mol_type = other DNA
                       organism = synthetic construct
misc_feature           1..28
                       note = synthetic
SEQUENCE: 9
aagtaggtat ccgtgagtgg tgtaatgt                                        28

SEQ ID NO: 10          moltype = DNA  length = 13
FEATURE                Location/Qualifiers
source                 1..13
                       mol_type = other DNA
                       organism = synthetic construct
misc_feature           1..13
                       note = synthetic
SEQUENCE: 10
cgacattaca cca                                                        13

SEQ ID NO: 11          moltype =   length =
SEQUENCE: 11
000

SEQ ID NO: 12          moltype =   length =
SEQUENCE: 12
000

SEQ ID NO: 13          moltype = DNA  length = 44
FEATURE                Location/Qualifiers
```

-continued

```
source                  1..44
                        mol_type = other DNA
                        organism = synthetic construct
misc_difference         36..43
                        note = n is a, t, c, or g
SEQUENCE: 13
aagtaggtat ccgtgagtgg tgtaagtaag tacggnnnnn nnnc                  44

SEQ ID NO: 14           moltype = DNA  length = 44
FEATURE                 Location/Qualifiers
source                  1..44
                        mol_type = other DNA
                        organism = synthetic construct
misc_difference         36..43
                        note = n is a, t, c, or g
SEQUENCE: 14
aagtaggtat ccgtgagtgg tgtaagtaag tacggnnnnn nnnc                  44

SEQ ID NO: 15           moltype = DNA  length = 70
FEATURE                 Location/Qualifiers
source                  1..70
                        mol_type = other DNA
                        organism = synthetic construct
misc_difference         32..39
                        note = n is a, t, c, or g
SEQUENCE: 15
aagtaggtat ccgtgagtgg tgagttatcg gnnnnnnnnc cgataactca ccactcacgg  60
atacctactt                                                         70

SEQ ID NO: 16           moltype = DNA  length = 70
FEATURE                 Location/Qualifiers
source                  1..70
                        mol_type = other DNA
                        organism = synthetic construct
misc_difference         32..39
                        note = n is a, t, c, or g
SEQUENCE: 16
aagtaggtat ccgtgagtgg tgagttatcg gnnnnnnnnc cgataactca ccactcacgg  60
atacctactt                                                         70
```

METHOD FOR MEDIUM-THROUGHPUT MULTI-SINGLE-CELL REPRESENTATIVE DNA METHYLATION LIBRARY CONSTRUCTION AND SEQUENCING

CROSS-REFERENCE TO RELATED APPLICATIONS

The present application is a continuation-in-part application of PCT application No. PCT/CN2022/073322 filed on Jan. 21, 2022, which claims the benefit of Chinese Patent Application No. 202110336815.7 filed on Mar. 25, 2021. The contents of all of the aforementioned applications are incorporated by reference herein in their entirety.

REFERENCE TO SEQUENCE LISTING

The Sequence Listing XML file submitted via the USPTO Patent Center, with a file name of "Substitute_Sequence_Listing_SCH-23136-USCIP", a creation date of Jan. 10, 2024, and a size of 18 KB, is part of the specification and is incorporated in its entirety by reference herein.

TECHNICAL FIELD

The present application relates to the technical field of DNA sequencing, and in particular to a set of barcode adapters and a construction and sequencing method for medium-throughput representation DNA methylation library of multiple single cells.

BACKGROUND

As a hot spot in the disease research, methylation is highly correlated to gene expression and phenotypic traits. DNA methylation in organisms refers to a process of transferring methyl group from S-adenosylmethionine (SAM) to a specific base as a methyl donor under catalysis of a DNA methyltransferase (DMT). DNA methylation could occur at an N-6 position of adenine, an N-7 position of guanine, a C-5 position of cytosine, etc. However, in mammals, it occurs mainly on cytosines of 5'-CpG-3' and results to produce 5-methylcytosine (5 mC). In mammals, there are two common patterns of CpG: (1) CpG dinucleotides are dispersed in DNA sequences; (2) CpG dinucleotides are highly aggregated, and hence forming the CpG islands. In a normal genome sequence of a mammal, 70% to 90% of dispersed CpGs are methylated, while the CpG islands are often in a non-methylation state (except for some special regions and genes). In addition, CpG islands are often located near the transcriptional regulation regions and are related to 56% of coding genes of the human genome. Therefore, it is very important to investigate the state of methylation on CpG islands in gene transcription regions.

Classical methods of DNA methylation sequencing: There are mainly three traditional methods for studying DNA methylation: (1) bisulfite-specific conversion of non-methylated cytosine (C) and bisulfite sequencing (BS); (2) specific binding of methylated or non-methylated C or the CpG DNA, such as methylated DNA immunoprecipitation (MeDIP) or specific binding and enrichment of a methylated binding protein (MeCP2); and (3) resistance of methylated DNA to a methylation-sensitive restriction endonuclease (Resistance to Methylation-sensitive Restriction Endonuclease, MRE). However, the BS, MeDIP, and MRE all require a considerably large amount of DNA samples for producing reliable reads. The BS method may allow accurate quantification and reach single-base level of resolution, and is a gold standard for DNA methylation analysis. Methods such as whole-genome bisulfite sequencing (WGBS) and reduced-representation bisulfite sequencing (RRBS) are most widely used for detecting methylation of CpGs and CpG islands in genomes of mammalian cell populations.

In recent years, researchers have developed the following novel techniques for investigating single-cell DNA methylation: single-cell whole-genome bisulfite sequencing (scBS/scWGBS) and single-cell reduced-representation bisulfite sequencing (scRRBS), as shown in FIG. 1.

In the scBS (or scWGBS), DNA released through cell lysis are first treated with a bisulfite, and then followed by library construction, amplification, and high-throughput sequencing (HTS), and determining a location of methylation and an affected gene. The scBS (or scWGBS) technique is capable of comprehensively covering about 48% of CpG sites of the whole genome. However, as mentioned above, because WGBS/BS randomly covers all bases of the whole genome, library sequencing is expensive, single-cell gene sequences are easy to lose, and a coverage degree is low and has low consistency. More importantly, scBS/scWGBS is not convenient for high-throughput library construction of de novo sequencing of a big number of samples.

scRRBS is obtained by improving the original RRBS, and before polymerase chain reaction (PCR) amplification, all experimental steps of a sample are integrated into a single-tube reaction. A library construction process of scRRBS is shown in FIG. 2. scRRBS is mainly characterized in that representative CpG sites in a single cell is detected with a small amount of sequencing data while allowing targeted coverage of methylated CpG islands. scRRBS has a lower cost and higher consistency of coverage degree than scBS (or scWGBS), is suitable for research on DNA methylation profiling such as for single-cell CpG islands, and is capable of achieving a single-base resolution.

In 2017, Xinghua Pan et al. (Han, L., et al. (2017) Bisulfite-independent analysis of CpG island methylation enables genome-scale stratification of single cells. Nucleic Acids Res, 45, e77.) published an analysis technique for BS-independent single-cell methylation: single-cell CpG-island sequencing (scCGI-seq). scBS (or scWGBS) and scRRBS experiments cause severe damage to DNA due to a bisulfite treatment. MRE (Methylation-sensitive restriction endonuclease) may directly cover CpG-island (CGI) methylation without a bisulfite treatment, and thus reduces a random loss of DNA. In the scCGI-seq technique, methylated CGI is distinguished from non-methylated CGI through digestion of MRE, and a long DNA strand including methylated CGI is selectively amplified by the multiple displacement amplification (MDA) technology, but a short DNA strand is not amplified. According to sequencing analysis of scCGI-seq, a genome-scale coverage degree is the same as a result of the BS technology, and the consistency of coverage degree is significantly improved (as shown in FIG. 3). This method is potential of being improved into a high-throughput technique; however, it has the drawback of failing to reach the single-base resolution.

Analysis of large number of single cells at epigenetic aspect is a necessary means for unraveling the mechanism of cell population heterogeneity. Single-cell RNA sequencing (scRNA-seq) may acquire data of thousands or tens of thousands of single cells at a time, and the single-cell sequencing for chromatin accessibility (scATAC-seq, single-cell sequencing assay for transposase-accessible chromatin) also has a corresponding high-throughput protocol. However, either scBS and scWGBS or scRRBS has disadvantages such as low efficiency, poor data quality, and high application cost, which greatly limit the application of these two techniques. Due to a high sequencing cost, in the research reports of single-cell methylation sequencing currently published, only a very small number of single cells are analyzed, and generally, only dozens of single cells are analyzed.

SUMMARY

Based on the above problems, an objective of the present application is to provide a set of barcode adapters to overcome the shortcomings of the scRRBS technique and to provide a medium to high-throughput method for simultaneously construction of library, and sequencing the library, for profiling CpG methylation in a plurality of single cells.

In order to well meet the research on heterogeneity for single-cell CpG methylation, the present application provides a novel multi-scRRBS (msRRBS) method based on early barcode tagging, and designs and tests of the alternative method thereof. In the alternative method, an APOBEC enzyme is used for converting non-methylated cytosine (C) instead of bisulfite conversion, and the alternative method is tentatively named multi-scRRAS (msRRAS). The present application is intended to provide a sequencing method suitable for CpG methylation analysis of large-scale single cells, which mainly focuses on analysis of CpG-rich sequences such as CpG islands and promoters and has advantages such as high throughput, low cost, and robust operations compared with the scBS (or scWGBS) and the scRRBS methods.

In order to allow the objective above, the technical solution adopted by the present application includes the following three major aspects: a set of barcode adapters, a detection method (namely, an experimental scheme), and a use.

In a first aspect, the present application provides a set of barcode adapters and corresponding primers for library construction of CpG methylation of single cells, where the barcode adapters each include a PCR amplification primer sequence, an associated sequence of a restriction endonuclease required for removal of primers in an amplification product, and a preset cohesive sequence for subsequent adapter ligation, a sample barcode sequence, and a cohesive end sequence of CG.

The barcode adapters are not capable of forming a dimer or a multimer with each other under an action of a ligase, but only form a triplet structure of “adapter+inserted DNA fragment+adapter” with a DNA fragment having a complementary cohesive terminus and a phosphate group at the 5' end. In addition, when the adapters at a relatively-high concentration coexist with DNA fragments at a low concentration, all DNA fragments are efficiently covered and produce triplets, and because the 5' end of a short oligonucleotide of a barcode adapter is blocked, including lack of a phosphorylated group, the 3' end of a genomic DNA (gDNA) fragment does not form a 3'-5' phosphodiester bond directly with a barcode adapter.

The barcode adapter may further include an index for an experimental batch and a sequence compatible with a sequencing library adapter sequence compatible with a specific next-generation and a third-generation sequencing platform.

In a particular embodiment, a base at each position in each of the set of barcode adapters and/or the index for the experimental batch is any one selected from the group consisting of A, T, C, and G, any one selected from the group consisting of 3 or 2 bases of A, T, C, and G, or a specific base.

In a particular embodiment, for the set of barcode adapters, different barcode adapters of the plurality of sequences each are composed of a short oligonucleotide and a long oligonucleotide; a Tm value of the short oligonucleotide needs to be higher than 10° C. and lower than 60° C., preferably higher than 14° C. and lower than 56° C., and more preferably higher than 14° C. and lower than 50° C.; and the short oligonucleotide and the long oligonucleotide are denatured and annealed to form a long-short double-stranded DNA adapter.

In a particular embodiment, for the set of barcode adapters, the long oligonucleotide includes a sample barcode sequence, an associated sequence for recognition of a restriction endonuclease required for primer removal, a preset cohesive sequence for subsequent adapter ligation, and a primer sequence for PCR amplification, sequentially from 5' end to 3' end.

In a particular embodiment, the set of barcode adapters, characterized in that the 3' end of the short oligonucleotide is modified by a group with a function of preventing ligation or polymerase extension, including, but not limited to, 3' dideoxycytidine (3'ddC), 3' inverted dT, 3' C3 spacer, 3' amino, and 3' phosphorylation and the like.

Preferably, the group with a function of inhibiting exonuclease enzymolysis is 3'ddT or 3' amino.

In a particular embodiment, there is a modification for stabilizing nucleotides to avoid degradation between any two or more nucleotides at the 5' end and/or the 3' end and the 1st to the 10th nucleotide positions proximal to the terminal of the set of barcode adapters; and preferably, the modification is a phosphorothioate modification.

In a particular embodiment, for the set of barcode adapters, the short oligonucleotide includes a cohesive terminus (5'-CG-3' in the case of MspI cleavage), a complementary sequence of a barcode sequence, and/or some other sequences, sequentially from 3' end to 5' end.

In a particular embodiment, for the set of barcode adapters, the long-short double-stranded DNA adapters each include a primer sequence for PCR amplification (an action of a 5' end sequence of an adapter).

In a particular embodiment, for the set of barcode adapters, the cytosine in the long oligonucleotide is cytosine modified by methylation (5 mC).

In a particular embodiment, for the set of barcode adapters, a base at each position in each of the oligonucleotides is any one selected from the group consisting of A, T, C, and G, any one selected from the group consisting of 3 or 2 bases of A, T, C, and G, or a specific base; and cytosine in the long oligonucleotide is cytosine modified by methylation.

In a particular embodiment, for the set of barcode adapters, a number of bases of the barcode sequence and/or the index for the experimental batch is 2 or more.

Preferably, the number of bases of the barcode sequence is 6, 8, or 10.

More preferably, the number of bases of the barcode sequence is 6.

In a particular embodiment, for the set of barcode adapters, the plurality of different barcode adapters have different barcode sequences.

In a particular embodiment, for the set of barcode adapters, the primer sequences for PCR amplification of different barcode adapters of the plurality of sequences are identical.

In a particular embodiment, for the set of barcode adapters, different barcode adapters of the plurality of sequences are compatible with PCR amplification primers, and are provided to capture/ligate and amplify genomic fragments.

In a particular embodiment, for the set of barcode adapters and the primer sequences are as follows: a long oligonucleotide sequence: 5' AAG TAG GTA TCmCm GTG AGT GGTG AAGAAT (SEQ ID NO: 1); a short oligonucleotide sequence: 5' CG ATTCTT CACCA/3Amino/(SEQ ID NO: 2); and one of the primer sequences: 5' AAG TAG GTA TCC GTG AGT GGTG (SEQ ID NO: 3).

In a particular embodiment, for the set of barcode adapters, the samples may be a single cell, a small number (micro-bulk) of cells, DNA extracted from an organ tissue.

In a particular embodiment, for the set of barcode adapters, the HTS platform is an Illumina sequencing platform HiSeq, NextSeq, MiniSeq, MiSeq, NovaSeq, or MGISEQ of Beijing Genomics Institute (BGI), or a third-generation sequencing platform such as PacBio or Nanopore.

In a particular embodiment, for the set of barcode adapters, the HTS platform is a high-throughput sequencer of Illumina HiSeq X Ten.

In a particular embodiment, the PCR amplification primers for the set of barcode adapters include an index for an experimental batch and an adapter sequence of a sequencing library compatible with a specific next-generation or/and a third-generation HTS platform, and do not include an enzyme-associated sequence for primer removal.

The present application provides a preparation method of the set of barcode adapters, and the preparation method is obtained by combining a plurality of barcode adapters with different sequences.

The plurality of barcode adapters with different sequences each are prepared by the following method: dissolving a short oligonucleotide and a long oligonucleotide in a TE buffer, conducting a reaction at 94° C., rapidly cooling a resulting reaction system to 80° C., then naturally cooling the reaction system to room temperature, and forming a barcode adapter in which partial bases are complementarily paired.

In a second aspect, on the basis of the adapters and primers described above, the present application provides a method for simultaneously detecting CpG methylation in a plurality of samples. The method is preferably suitable for medium to high-throughput library construction and sequencing, and includes the following steps:

(1) independently lysing the plurality of samples to release respective gDNAs;
(2) purifying the released gDNAs or proceeding directly to the next step without purifying the released gDNAs;
(3) fragmenting the released gDNAs or purified gDNAs to obtain DNA fragments of different lengths;
(4) ligating a DNA fragment of each of the samples to a barcode adapter with a different barcode, respectively;
(5) pooling DNA fragments of the plurality of samples that are ligated with a barcode adapter to obtain a DNA fragment pool;
(6) subjecting the DNA fragment pool to repair of barcode adapters with a DNA polymerase to construct complete barcode adapters;
(7) converting non-methylated cytosine in DNA fragments with complete barcode adapters;
(8) subjecting converted DNA fragments to a first round of polymerase chain reaction (PCR) amplification, the amplification being conducted using primers compatible with barcode adapters (such as the primer J10P4);
(9) removing a primer sequence at an end of a DNA fragment after the first round of PCR amplification according to a restriction endonuclease-associated sequence for primer excision and employing a corresponding restriction endonuclease, retaining a barcode sequence in the DNA fragment, and recovering DNA fragments;
(10) ligating the DNA fragments recovered in step (9) to adapters with primers for a second round of PCR amplification, sequences of the adapters with primers for a second round of PCR amplification being compatible with a specific next-generation or/and a third-generation HTS platform;
(11) subjecting a ligation product of step (10) to selection of fragment lengths, enrichment or recovery, and purification to obtain a preliminary library suitable for lengths of the sequencing platform;
(12) subjecting a ligation product obtained in step (11) to the second round of PCR amplification, where the 3' primer includes a batch index, and a primer pair used for the amplification is compatible with the specific next-generation or third-generation sequencing platform;
(13) subjecting an amplification product of step (12) to selection of fragment lengths, enrichment or recovery, and purification to obtain a library suitable for the lengths of the sequencing platform;
(14) sequencing the library obtained in step (13) with the specific next-generation or third-generation sequencing platform to obtain methylation data for the pooled plurality of samples; and
(15) decoding the methylation data obtained in step (14) through information analysis to obtain methylation patterns of each batch and each sample.

Further, in step (3), the gDNAs are cleaved with a restriction endonuclease to allow DNA fragmentation; the restriction endonuclease is not sensitive to methylation, and 50% or more of bases of a recognition sequence for the restriction endonuclease are composed of C and G; and preferably, the recognition sequence has a length of 4 bases, and the 4 bases all are C and G and include at least one CG di-nucleotide.

Preferably, in step 3), the DNA fragmentation is conducted such that short fragments have a relatively-high CG content, or gDNA sequences with a relatively-high CG content are enriched into short fragments; the short fragments refer to DNA fragments with a length of no more than 700 bp; and the DNA fragments with a relatively-high CG content refer to DNA fragments in which a proportion of nucleotides C and G exceeds 50% and preferably 60%, 70%, 80%, or 90%.

More preferably, 60%, 70%, 80%, or 90% or more of bases of the recognition sequence are composed of C and G.

Preferably, the restriction endonuclease in step (3) is a Type II restriction endonuclease capable of producing a cohesive terminus rather than a blunt terminus; and the cleavage is conducted through an independent action of one restriction endonuclease or a combined action of two or more restriction endonucleases, and preferably, the one restriction endonuclease is MspI.

Preferably, the barcode adapter in step (4) includes a short oligonucleotide and a long oligonucleotide or is composed of a short oligonucleotide and a long oligonucleotide; the long oligonucleotide includes a partial primer sequence for PCR amplification, a Type IIs restriction endonuclease recognition sequence required for primer removal, a cohesive terminus-associated sequence of a preset adapter, and a sample barcode sequence, sequentially from 5' end to 3' end; and the short oligonucleotide includes a cohesive terminal sequence and a complementary sequence of the sample barcode sequence, sequentially from 5' end to 3' end.

Preferably, the barcode adapter includes a cohesive terminal sequence, a sample barcode sequence, a primer-associated sequence for PCR amplification, and a primer; the barcode adapters are designed to capture gDNA fragments and directly ligate the gDNA fragments; and the barcode adapter facilitates the high-throughput conversion of multiple samples and the amplification of cohesive terminus-containing gDNA fragments without forming adapter dimers, and are used for sequencing library construction of representative CpG methylation.

Preferably, a Tm value of the short oligonucleotide is higher than 10° C. and lower than 60° C., and preferably, the Tm is higher than 14° C. and substantially lower than 56° C. (such as 14° C.<Tm<50° C.); and the 5' end of the short oligonucleotide is blocked through preset modification to form a phosphodiester bond with 3' end hydroxyl (3'-hydroxyl) of any DNA fragment, and preferably, the 5' modification refers to lack of a 5'-phosphate group (free of 5'-phosphate).

Preferably, the short oligonucleotide and the long oligonucleotide are denatured and then annealed to produce a long-short double-stranded DNA adapter; and an end of the long-short double-stranded DNA adapter corresponding to the 3' end of the long oligonucleotide is cohesive and is complementary to a cohesive terminus of CpG-enriched fragmented DNA.

Preferably, a protruding sequence of a cohesive terminus of the short oligonucleotide is 5'CG; the 5'CG is correspondingly paired with a cohesive terminus produced after cleavage of DNA by a restriction endonuclease MspI, and is unable to form a phosphodiester bond with a cohesive terminus produced after cleavage of DNA by MspI or a cohesive terminus of another double-stranded DNA adapter due to lack of a 5'-phosphate group in 5'C of the 5'CG.

Preferably, the restriction endonuclease is MspI; the protruding sequence of the cohesive terminus of the short oligonucleotide is 5'CG, and the 5' CG may be complementary to the 3' end of the long oligonucleotide to produce a cohesive terminus, but due to absence of a phosphorylated group in the 5' end nucleotide, this end does not form a stable structure of a phosphodiester bond with the 3' end of any DNA fragment (a DNA fragment obtained after enzyme cleavage, or a double-stranded adapter composed of itself-a long oligonucleotide and a short oligonucleotide). Therefore, no dimer of such double-stranded adapters stably exists in a ligation mixture, and if there is not a subsequent further treatment, a corresponding amplification product is not present.

Preferably, the 3' end of the short oligonucleotide is modified by a group with a function of preventing ligation or polymerase extension; and the group modification is 3' dideoxycytidine (3'ddC), 3' inverted dT, 3' C3 spacer, 3' amino, or 3' phosphorylation, and is preferably 3'ddC or 3' amino.

Preferably, a base of a deoxynucleotide at each position of the short oligonucleotide and the long oligonucleotide is any one selected from the group consisting of A, T, C, and G, or any one selected from the group consisting of 3 bases of A, T, C, and G, or any one selected from the group consisting of 2 bases of A, T, C, and G, or a specific base.

Preferably, the cytosine in the long oligonucleotide is methylated cytosine (5 mC).

Preferably, a number of bases of the sample barcode sequence is 2 to 10, preferably 4 to 8, and more preferably 6.

Preferably, the plurality of different barcode adapters have different barcode sequences, and primer sequences for PCR amplification of the plurality of barcode adapters with different sequences are identical.

Preferably, in the barcode adapter, a Type IIs restriction endonuclease preset for primer removal after amplification and a cohesive terminus-associated sequence of a preset adapter are inserted between a barcode sequence and a PCR primer, and after cleavage of the restriction endonuclease, 1 base protruding at the 3' end or the 5' end is formed; and the restriction endonuclease may be inactivated by heating.

Preferably, the Type IIs restriction endonuclease is BciVI.

Preferably, the recognition sequence for the restriction endonuclease is 5'-GTATCCNNNNNNT-3' (SEQ ID NO: 4), where N is any one selected from the group consisting of A, T, C, and G.

Preferably, there is a modification for stabilizing nucleotides and preventing the nucleotides from degradation by a nuclease between any two adjacent nucleotides in the barcode adapter, and more preferably, the modification is a phosphorothioate modification. Preferably, there is a modification between the 5' end and/or the 3' end and the 1st to the 5th nucleotides proximal to the terminal of the barcode adapter; and more preferably, there is a modification between the 1st to the 3rd nucleotides proximal to the terminal.

Preferably, a sequence of the long oligonucleotide is 5'AAG TAG GTA TCmCm GTG AGT GGTG AAGAAT (SEQ ID NO: 1).

Preferably, a sequence of the short oligonucleotide is 5'CG ATTCTT CACCA/3Amino/(SEQ ID NO: 2).

Preferably, the primers for PCR amplification include an index for an experimental batch and an adapter sequence of a sequencing library compatible with a specific next-generation or/and a third-generation HTS platform, and do not include an enzyme-associated sequence for primer removal.

More preferably, a sequence of one of the primers (J10P4) used for the first round of PCR amplification in step (8) is 5'AAGTAGGTATCCGTGAGTGGTG (SEQ ID NO: 3).

Preferably, the samples are single cells, a micro-bulk of cells, or extracted and purified DNA.

Preferably, the specific next-generation HTS platform is an Illumina sequencing platform HiSeq, NextSeq, MiniSeq, MiSeq, NovaSeq, or MGISEQ of Beijing Genomics Institute (BGI), or a third-generation sequencing platform such as PacBio or Nanopore. More preferably, the HTS platform is a high-throughput sequencer of Illumina HiSeq X Ten.

Preferably, the repair of barcode adapters in step (6) is conducted with a template-dependent DNA polymerase, and the template-dependent DNA polymerase has no activity of strand-displacement and no nicking activity. The DNA polymerase has an activity of base displacement (strand displacement) or no activity of base displacement. More preferably, the template-dependent DNA polymerase is *Sulfolobus* DNA polymerase IV. More preferably, nucleotides used for the repair of barcode adapters in step (6) are four types of mononucleotides: deoxyguanosine triphosphate (dGTP), deoxyadenosine triphosphate (dATP), deoxythymidine triphosphate (dTTP), and 5mdCTP (i.e., 5 mC), where the 5mdCTP refers to cytosine modified by methylation (5 mC), which may ensure that sequences of barcode and adapter primers remain unchanged after conversion.

Preferably, the DNA fragments recovered in step (9) are 175 bp to 800 bp, preferably 175 bp to 550 bp, and more preferably 175 bp to 350 bp; and more preferably, 2 size ranges of DNA fragments with lengths of 175 bp to 350 bp and 350 bp to 550 bp respectively are recovered separately and then sequenced, and the sequencing data of the 2 size ranges of DNA fragments recovered separately are merged.

Preferably, the DNA fragments obtained in step (3) have a length of 30 bp to 2,000 bp, preferably 30 bp to 700 bp, more preferably 30 bp to 300 bp, and most preferably 30 bp to 200 by or 60 by to 300 bp.

Preferably, the cell lysis for releasing DNAs in step (1) includes adoption of a physical method, a chemical method, or an enzymatic hydrolysis method, where the chemical method includes, but not limited to, an ionic detergent and a non-ionic detergent such as sodium dodecyl sulfate (SDS), sarkosyl or sarcosyl, Triton X-100, Tween 20, and Tween 80.

Preferably, the DNAs in step (1) include gDNAs released from single cells or a plurality of cells or gDNAs extracted from tissue organs.

Preferably, in step (2), the gDNAs are subjected to the most basic purification, which is mainly intended to remove components inhibiting a downstream reaction; and a method for purifying the DNAs includes absolute ethanol co-precipitation and magnetic beads enrichment.

Preferably, a method for the fragmentation in step (3) includes a physical method, a chemical method, or an enzyme cleavage method via a methylation-insensitive Type II restriction endonuclease.

Preferably, the enzyme cleavage method via a methylation-insensitive restriction endonuclease is used to fragment the DNAs and enrich CG-rich regions, and preferably, MspI with a 4-base recognition site (CCGG), followed by TaqI, or other enzymes such as AluI, BfaI, HaeIII, HpyCH4V, MluCI, MseI, may also be a methylation-insensitive restriction endonuclease with a 5 to 6-base recognition sequence even an 8-base recognition sequence, or each equal portion of cells of a same sample are treated with two or more enzymes; and accordingly, a sequence of a cohesive terminus of an adapter composed of a long oligonucleotide and a short oligonucleotide should be adjusted to complement it, and a length of the DNA fragment recovered should be adjusted for efficiently recovering the library length fitting the fragmentation method and the sequencing platform.

As an alternative solution, a methylation-insensitive restriction endonuclease with a 5 to 6-base or even an 8-base recognition sequence and a high CG content is used to enrich CGI sequences; correspondingly, the DNA fragments recovered and enriched in step (3) have a length of 0.5 kb to 5 kb or more; and accordingly, the third-generation sequencing technology such as PacBio and its associated primers may be used to sequence such long fragments.

Preferably, in step (4), the barcode adapter is selected from the set of barcode adapters; and the ligation method is conducted with a DNA ligase, and a Fast-Link™ DNA Ligation Kit is preferred.

Preferably, in step (5), no less than 2, 96, 384, or more than 384 samples are pooled, and correspondingly, the pooling is conducted in a PCR multi-line tube or on a microplate or a customized microplate.

Preferably, the conversion in step (7) comprises bisulfite conversion and enzymatic conversion.

Preferably, the enzymatic conversion refers to a conversion method based on the APOBEC enzyme, including, but not limited to, an APOBEC enzyme and a buffer based on an NEB Next Enzymatic Methyl-seq Kit (EM-Seq™).

Preferably, the number of PCR amplification cycles in step (8) varies according to the quality of DNA and the number of samples.

Preferably, the methods for the fragment removal, which is the removal of extraneous primer portion sequences, in step (9) include physical methods, chemical methods, or enzymatic hydrolysis methods; and more preferably cleavage by BciVI enzyme.

Preferably, the ligation in step (10) is conducted with a DNA ligase and preferably a Fast-Link™ DNA Ligation Kit; and the ligated primer adapter is single-stranded or double-stranded and preferably is double-stranded.

Preferably, the preliminary sequencing library or/and the final sequencing library in steps (11) (13) are/is conducted with recovery of sequences with a specified length; a method for the recovery of sequences with a specified length is gel electrophoresis, magnetic beads capable of sorting DNA lengths, or high-performance liquid chromatography (HPLC); the gel electrophoresis is preferably conducted with 2% E-Gel; and the magnetic beads are preferably AMPure XP Beads.

Preferably, the preliminary sequencing library in step (11) is conducted with purification or recovery of sequences with a specific length (including a primer and an adapter); and the length of specific sequences recovered is 120 bp to 1,000 bp, preferably 120 bp to 500 bp, more preferably 120 bp to 400 bp, and most preferably 120 bp to 300 bp or 150 bp to 390 bp.

Preferably, the final sequencing library in step (13) is conducted with purification or recovery of sequences with a specific length (including library adapters); and the length of specific sequences recovered is 170 bp to 1,000 bp, preferably 170 bp to 800 bp, more preferably 170 bp to 500 bp, further more preferably 170 bp to 400 bp, and most preferably 170 bp to 350 bp or 200 bp to 440 bp.

Preferably, the sequencing platforms in steps (11), (12), (13), (14) are Illumina sequencing platform HiSeq, NextSeq, MiniSeq, MiSeq, NovaSeq, or MGISEQ of Beijing Genomics Institute (BGI), or third-generation sequencers such as Nanapore, PacBio, and is preferably a high-throughput sequencer of Illumina Hiseq X Ten, and paired-end or single-end sequencing, and preferably, a length of the paired-end sequencing is 150 bp.

More preferably, the paired-end or single-end is conducted for sequencing of different lengths.

Preferably, the information analysis for decoding the sequencing data in step (15) includes the following steps:

1) pre-processing the methylation data of step (14), including distribution and quality control of ligated indexes and barcode data, and removal of sequencing adapters and low-quality bases; and
2) aligning sequencing data obtained after the pre-processing in step 1), subjecting alignment results to quality control, calculating the conversion rate, detecting the number of methylation CpG sites and CGIs, and conducting evaluation of Pearson correlation coefficient, methylation pattern analysis, correlation analysis, differential methylation analysis, and enrichment analysis.

Preferably, the DNA fragments from different samples in step (15) are ligated to different next-generation sequencing (NGS) adapters, respectively, and then sequencing is conducted.

The present application also covers automated and semi-automated electromechanical instruments related to some or all treatments in steps including sample sorting, sample addition, and library preparation.

In a third aspect, the present application provides use of the primer set, kit, related device, or sequencing method in fields including biological sciences research, medical research, clinical diagnosis, or drug research and development, and in agriculture, plant, animal, and microorganism research, including, but not limited to, development, tumors, immunity, genetic diseases, experimental targeting, viruses, animal husbandry, traditional Chinese medicine (TCM), and drug research and development.

The novel method provided by the present application, named msRRBS (an alternative solution msRRAS is similar to this method, the same at below), simplifies the operating procedures and reduces the damage to DNA and adapters during enzymatic and chemical treatments; and in the novel method, different samples (preferably single cells) are pooled immediately after a specific barcode is added to each cell with a minimal treatment at a very early stage, and the operation is completed in a single test tube, which allows a high degree of multiplicity (high throughput). Since a large number of samples (or single cells) may be manipulated at a time, the method (when a large number of samples or single cells are manipulated) may greatly reduce the complexity of library construction, improve the consistency of different single cell operations in a same batch, greatly reduce the experimental cost and DNA damage, and improve the coverage degree and the consistency of experimental results.

Compared with the traditional scRRBS method, the msRRBS method mainly has the following advantages: (1) Efficient operations: An operator may construct a library simultaneously for 96, 384, or more or less single cells (or multi-cell samples, or DNA samples) in a reaction system at a time, where the number of cells mainly depends on the type number of barcodes (The sequence structure and description of the barcode are shown in FIG. 6) and a cell sorting platform; single-cell methylation data involving a large number of single cells may be obtained through NGS; and finally, bioinformatics analysis may be used to determine the DNA methylation profile of each cell. Obviously, compared with the previous scRRBS, the novel method msRRBS allows library construction for a large number of single cells (flexible arrangement) at a time, which leads to high efficiency, greatly reduces the time consumption, and simplifies the operation procedures. Although some researchers (including ourselves) have tried to establish a multi-RRBS method with an index-containing long adapter of conventional Illumina NGS as an adapter for each single cell, successful cases have been rarely reported, which is attributed to the following reasons: the above conventional adapter is too long and thus has a high risk of breaking during BS conversion, which makes the recovery of the fragment fail; and the conventional ligation requires a process of multi-enzymatic modification of the DNA fragments obtained after enzymatic cleavage of a very small amount of DNA in advance, and a corresponding enzymatic reaction also leads to DNA damage. We have also tested a double-stranded adapter connected by a covalent bond that may be directly ligated to a fragment obtained after enzyme cleavage of DNA. Because a CG cohesive terminus produced by MspI often leads to preferential ligation of adapters to each other due to a large quantity, and the formation of a large number of adapter dimers seriously inhibits the effective ligation of an adapter to a DNA fragment, thereby resulting in the failure of an experiment. The present application overcomes the 3 key problems. (2) Low cost: A main process of methylation sequencing for single cells is as follows: acquisition of single cells, library construction, HTS, and data analysis. The library construction involves more than ten steps, and the required cost, time, and an operation process of the library construction vary greatly. The traditional scRRBS method only allows library construction for a single cell in a same reaction system; with basically the same cost, the method msRRBS of the present application allows library construction for tens or even hundreds of single cells in parallel, that is, all cells are pooled immediately after a specific barcode is added to each cell with a minimal treatment for cells at the early stage, and the operation is completed in a single tube, which greatly reduces the experimental cost. (3) Excellent and consistent coverage: after being treated by a special method (See description as shown in FIG. 6), the specially designed barcode adapter is directly ligated to the DNA fragments, which reduces the loss of DNA sequences caused by adapter breaking, thereby significantly improves the coverage of DNA sequences. (4) Fewer variations in technical operations: Due to reduction of treatments and batch operations, the consistency of sample processing is guaranteed, which reduces or avoids operational differences among samples. Therefore, the msRRBS method has great advantages in the research of single-cell DNA methylation.

Compared with the scRRBS, the msRRBS has both common aspects and novel aspects in terms of principles. Common aspects: In both of the two methods, the restriction endonuclease MspI (or other frequency cleavage enzymes in CG-rich restriction endonucleases that are insensitive to CpG methylation modification, and generally 4 bases, no more than 6 bases) is used to cleave single-cell gDNA into DNA fragments for enriching sequences of methylated CpG islands. Novel aspects: In early experimental steps of the present application, a specifically designed short adapter containing a barcode with a tagging function, instead of a long adapter (barcode adapter), is directly ligated to an end of a single-cell gDNA fragment obtained after enzyme cleavage, without a DNA treatment (end-filling and an enzymatic reaction for adenine (A) addition are not required). After the first round of amplification, the unnecessary PCR amplification primer/adapter portion is removed, and a conventional adapter for a sequencing library compatible with the next-generation or third-generation sequencing platform used is ligated, such that the technology of the present application has excellent adaptability. Even if a novel sequencing platform is provided in the future, the present application may easily adjust a final adapter sequence of a library for adapting to the novel sequencing platform. In addition, the present application for the first time uses an APOBEC protein (including, but not limited to, an enzymatic conversion method of APOBEC based on an NEB Next Enzymatic Methyl-seq (EM-seq) reagent) to convert non-methylated C in a CpG di-nucleotide into U, which changes the traditional bisulfite conversion method and thus reduces the damage to gDNA, and is used in combination with other designs of the present application.

Compared with the long sequencing adapter (index adapter) used in the scRRBS technology, the direct ligation of a short adapter to a DNA fragment obtained after enzyme cleavage in the present application has the following advantages:

(1) The short adapter designed in the present application includes a barcode sequence (barcode adapter), and has a major function of specifically tagging all DNA fragments of each single cell (or each sample, the same at below) obtained after enzyme cleavage, that is, all DNA fragments of each cell are tagged by a same barcode-containing short adapter; tagged ligation products of different single cells after early tagging may be directly pooled in a same test tube for methylation conversion, amplification, and other library construction operations; and finally, NGS is conducted, and bioinformatics analysis may be used for classifying DNA fragments of different single cells into their respective cells according to different barcode types, which allows the detection and analysis of methylation of a large number of single cells through parallel experiments.

(2) The short barcode adapters designed in the present application may be directly ligated to DNA fragments obtained after enzymatic cleavage. Firstly, the latter does not require phosphorylation filling and addition of A (adenine) under an action of various enzymes in advance, which reduces the enzymatic operation and DNA damage and also improves the ligation efficiency. Secondly, an adapter repair process includes an appropriate high-temperature treatment to make the short adapter fragment melt and fall off, and efficient synthesis of a full-length new strand that is completely complementary to a long oligonucleotide adapter under guidance of *Sulfolobus* DNA polymerase IV; and during this process, the added methylated dCTP ensures that the base does not change a sequence during subsequent conversion. Thirdly, compared with the Illumina conventional adapter, the short adapter of the present application has a low risk of breaking, which greatly reduces the loss of DNA fragments.

(3) The barcode adapter above does not contradict the existing long sequencing adapter of Illumina NGS and the Index system, but is complementary thereto. The short adapter is ligated immediately after each single-cell DNA is cleaved by an enzyme; after methylation conversion, DNA is amplified by PCR; the extraneous primer portion is removed by BciVI; and then the long adapter of the conventional sequencing library is added, and a second round of amplification is conducted. The combination of the two greatly increases the throughput of library construction and sequencing and the scientificity of analysis. For example, the barcode adapter may distinguish among different single cells (or multi-cell samples, or DNA samples), and the library index may tag different batches of samples (technical replicates).

The present application is intended to overcome the shortcomings of scRRBS such as low efficiency, high cost, low and inconsistent coverage degrees for CpG island sequences, and large variation in experimental operations, and finally allows the scientificity of extensive application of single-cell CpG methylation and the feasibility of analysis of a large number of single cells.

The Present Application has the Following Advantages:

(1) Efficient operation process: An operator may construct a library simultaneously for 96, 384, more or fewer cells (the number of cells mainly depends on the type number of barcodes) in a reaction system at one time. A same type of cells may also be tagged with different indexes (cell specificity, that is, batch-specific tagging), which is convenient for comparison of batch effects, technical replicates, biological replicates, times, dose effects and controls, and other systematic operations of samples, and also facilitates the determination of increased single cells for a same sample. Single-cell methylation data involving a large number of single cells may be obtained through NGS; and finally, bioinformatics analysis may be used to determine the DNA methylation of each cell.

(2) Low-cost library construction: The traditional scRRBS technology requires a lot of time and consumes a large amount of reagents. On the other hand, with basically the same cost of a single cell, in the novel msRRBS technology, a large number (tens to hundreds) of different single-cell samples are pooled immediately after the DNA fragments of each single-cell are tagged by a barcode at a very early stage, such that library construction may be conducted for hundreds (or even more) of single cells at a time. This batch library construction greatly reduces the experimental cost because the main reagents and operation time are reduced tens or even hundreds of times.

(3) High data quality: The novel technical process reduces the treatments for a sample and increases a total DNA amount during DNA conversion, thereby reducing the damage and loss of DNA. The design of the novel adapter and ligation method facilitates the high-throughput treatment of a large number of samples, thereby improving the consistency of sample treatments and reducing or avoiding significant differences in coverage among samples.

BRIEF DESCRIPTION OF THE DRAWINGS

FIG. 4 shows a short adapter produced through a special treatment of a long oligonucleotide sequence: 5' AAG TAG GTA TCmCm GTG AGT GGTG AAGAAT (SEQ ID NO: 1) and a short oligonucleotide sequence: 5' CG ATTCTT CACCA/3'ddC/(SEQ ID NO: 2), where "3Amino" indicates that the 3' end of oligo1 is modified by amino, and the underlined "GC" represents a protruding sequence of a cohesive terminus;

FIG. 10A-FIG. 10D are images acquired by an E-Gel imager during pooling of library construction for 16 single cells of a cell line K562 (human chronic myelogenous leukemia cell line), and a K562 sample, Nuclease-Free Water, and DNA Maker from left to right; wherein FIG. 10A is an image acquired by the E-Gel imager for the first round of PCR; FIG. 10B is an image acquired by the E-Gel imager for gel recovery after the first round of PCR; FIG. 10C is an image acquired by the E-Gel imager for the second round of PCR; and FIG. 10D is an image acquired by the E-Gel imager for gel recovery after the second round of PCR;

DETAILED DESCRIPTION

The Principles of the Present Application are as Follows:

Based on the current scRRBS, (1) Single-cell gDNA is specifically cleaved into fragments by a restriction endonuclease MspI, a barcode adapter with a tagging function is directly ligated to termini of different single-cell DNA fragments, and DNA fragments of a plurality of single-cell samples are pooled in a same reaction system. (2) After methylation conversion of DNA sequences (non-methylated C in CpG of a fragment is converted into U, and methylated C remains the original methylation state), single-cell gDNA fragments are subjected to a first round of PCR amplification, and then the original adapter is removed through enzyme cleavage with a barcode sequence retained; a sequencing adapter is ligated, and a second round of PCR amplification is conducted; and then a specific index is added to each sample, and the library construction is completed. (3) After NGS, bioinformatics analysis is used to classify DNA fragments of different single cells according to different barcode types and distinguish among sample batches according to indexes, thereby analyzing the methylation of a large number of single cells.

Figure 8:
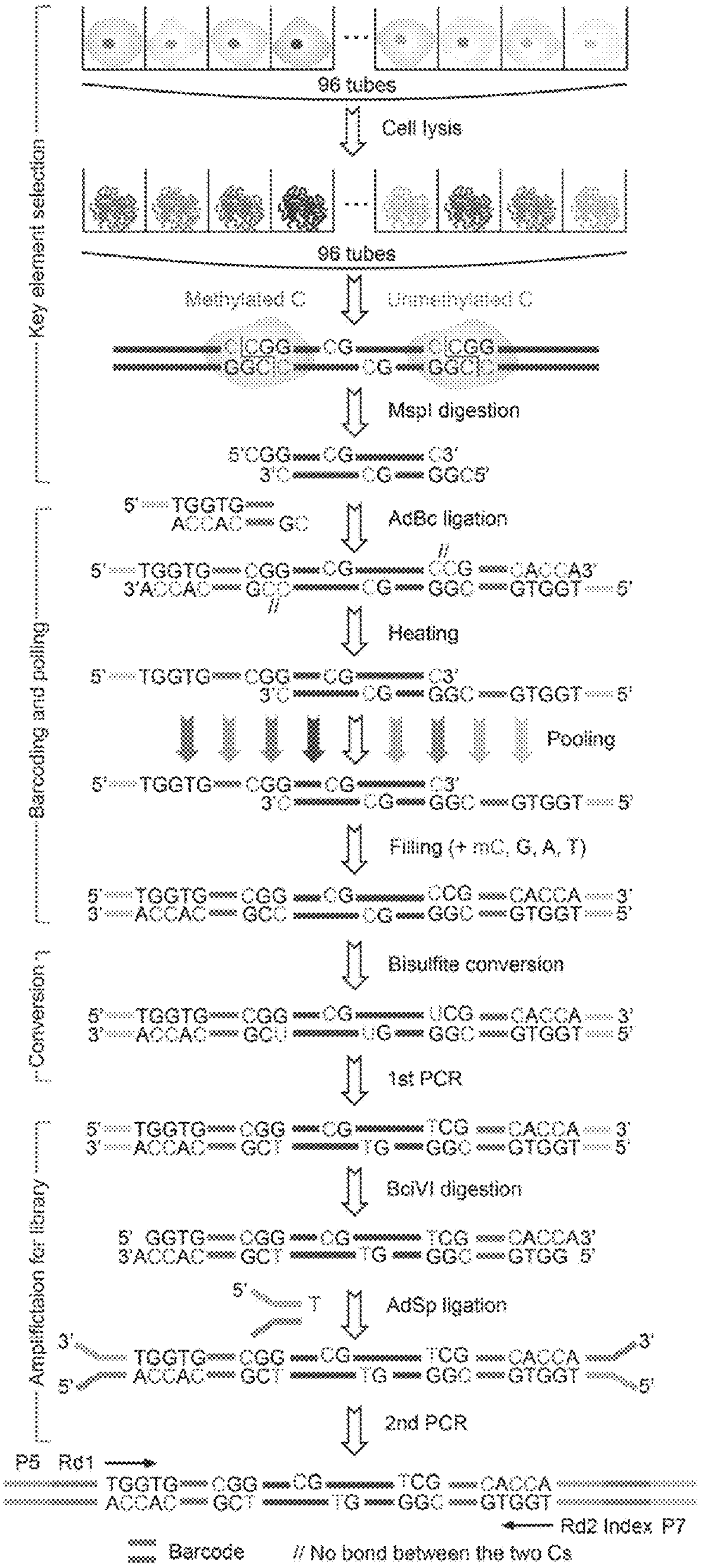
FIG. 8 is a complete schematic flow chart of the library construction method of the present application.

The detection method of the present application mainly includes the following steps (See FIG. 8): (1) single-cell lysis; (2) purification or non-purification of gDNA; (3) MspI cleavage; (4) ligation of a long-short double-stranded DNA adapter with a barcode; (5) pooling of DNA fragments of different single-cell gDNA fragments; (6) construction of a complete adapter; (7) conversion of non-methylated cytosine; (8) a first round of PCR amplification of DNA fragments; (9) removal of an adapter of the first round of amplification through BciVI cleavage and retaining of a barcode; (10) ligation of an NGS adapter; (11) electrophoresis separation, and purification and recovery of a target fragment with a gel; (12) a second round of PCR amplification of DNA fragments including sample indexes; (13) electrophoresis separation, and purification and recovery of a target DNA fragment with a gel; and (14) quality control and sequencing.

Unless otherwise specified, the reagents, materials, or cells used in the present application are commercially available.

Embodiment

A construction and sequencing method for medium-throughput representation DNA methylation library of multiple single cells was provided, including the following steps:

(1) Single-cell lysis: 4 μL of a 1×GC lysis buffer (Zymo) was added to each of PCR tubes with single cells, and the cells were lysed at room temperature for 15 min to fully release gDNAs. Since the single cells have a very low content of gDNAs, the cells must be completely lysed for releasing DNAs in this step. At 7.5 min of the lysis, the PCR tubes were flicked a few times by fingers (notes: the PCR tubes should not be shaken violently during the lysis, for example, suspensions in the PCR tubes should not be pipetted up and down to avoid breaking of gDNAs). The lysis may be conducted in a variety of other ways, such as Qiagen Protease.

(2) Purification of gDNAs: After a cell is completely lysed, in addition to gDNA, other substances are also released in a solution. Therefore, it is necessary to purify gDNA to remove components that may inhibit a downstream reaction. DNA was purified by an ethanol precipitation method. The reagents in Table 1 were added sequentially, and a resulting mixture was thoroughly mixed, placed in a −20° C. refrigerator to stand for 10 min, and then centrifuged by a high-speed refrigerated centrifuge at 13,300 rpm or more and 4° C. for 15 min; after the centrifugation was completed, a resulting supernatant was discarded, 200 μL of 80% ethanol (pre-cooled at −20° C.) was added to the PCR tube, and the PCR tube was then centrifuged at 10,000 rpm and 4° C. for 10 min; and finally, a resulting supernatant was discarded, a cap was removed, and a resulting precipitate was air-dried. If Qiagen protease is used, no purification is required, and it only needs to inactivate Qiagen protease through heating according to instructions.

TABLE 1

| Purification reagents | |
|---|---|
| Nuclease-Free Water | 26 μl |
| Qiagen Carrier RNA polyA (1 μg/μl) | 1 μl |
| Dr. GenTLE Precipitation Carrier | 4 μl |
| Sodium acetate | 4 μl |
| 100% Ethanol (−20 °C) | 112 μl |

(3) MspI cleavage: An MspI enzyme was used to specifically cleave single-cell gDNA to obtain DNA fragments of different lengths. The reagents in Table 2 were added sequentially to the PCR tube, and a resulting mixture was thoroughly mixed and then placed in a PCR instrument, and an reaction condition of enzyme cleavage was: 37° C. (the hot cap temperature was 50° C.) for 2.5 h (roles of carrier DNA: replace gDNA, be digested by excessive enzyme, and avoid damage to gDNA; and a role of non-methylated λDNA: detecting a conversion efficiency of completely unmethylated C by a methylation conversion treatment).

TABLE 2

| Enzyme cleavage reagents | |
|---|---|
| Nuclease-Free Water | 0.1 μl |
| ARF35 (Carrier DNA, 1 μg/μl) | 1 μl |
| Tango Buffer (10×) | 0.3 μl |
| Msp I (10 unit/μl) | 0.6 μl |
| Unmethylated lambda-DNA (60 fg/μl) | 1 μl |

(4) Ligation of a barcode adapter: Different types of barcode adapters were ligated to different single-cell DNA fragments, respectively, that is, each single cell corresponded to a barcode. The reagents in Table 3 were added sequentially to the PCR tube, and a resulting mixture was thoroughly mixed and placed in a PCR instrument, then a ligation reaction was allowed at 25° C. for 20 min, at 16° C. for 14 h, and at 25° C. for 20 min (the hot cap temperature was 50° C. in this step); and then enzyme inactivation was conducted at 75° C. for 15 min (the hot cap temperature for the inactivation was 90° C.). A sample was placed on an ice box immediately after the ligation was completed, and centrifuged at 10,000 rpm for 10 s to collect wall beads. 1 μL of EDTA diluted to a concentration of 125 mM was added to each reaction tube, and a resulting mixture was thoroughly mixed and then incubated on a PCR instrument at 37° C. for 15 min with a hot cap temperature of 50° C.

TABLE 3

| Ligation reagents of barcode adapters | |
|---|---|
| (Barcode adapter) (0.01 nmol/μL) | 0.3 μl |
| ATP (10 mM) | 0.6 μl |
| 10× Fast Link Ligation Buffer | 0.3 μl |
| Fast-Link ™DNA Ligation kit | 0.2 μl |
| Nuclease-Free Water | 0.6 μl |

(5) Pooling of gDNA fragments of different single cells: After the different single cells were tagged by different types of barcodes, all single-cell samples were pooled into a same reaction system (PCR tube). AMPure XP Beads were added to the PCR tube with pooled samples in a volume 1.5 times a solution in the PCR tube (the magnetic beads should be thoroughly shaken and then stand at room temperature for 15 min before use), and a resulting mixture was thoroughly mixed and then allowed to stand at room temperature for 15 min; then the PCR tube was placed on a magnetic separator and allowed to stand for at least 5 min until a resulting solution was clear, and a resulting clear solution was discarded (this step was conducted on the magnetic separator with a tip not touching the magnetic beads); 200 μL of 80% ethanol (which was prepared just before use) was added, a resulting system was allowed to stand for 30 s, and a resulting clear solution was discarded (this step was repeated twice); then the PCR tube was removed from the magnetic separator and air-dried naturally for about 5 min, 19 μL of Nuclease-Free Water was added to the PCR tube, and the magnetic beads in the tube were gently pipetted up and down about 10 times and then allowed to stand at room temperature for 2 min; and finally, the PCR tube was placed on a magnetic separator and allowed to stand for 2 min, and 18 μL of a DNA-containing clear solution was pipetted to a new PCR tube.

(6) Construction of a complete adapter: An adapter was repaired to obtain a complete double-stranded adapter. The reagents in Table 4 were added sequentially to the PCR tube, and a resulting mixture was thoroughly mixed and placed in a PCR instrument, and the reaction conditions were: 55° C. for 30 min (the hot cap temperature was required at 105° C.) (notes: ① the pooling of samples and reagents should be conducted on ice; and ② the reaction requires hot initiation, that is, the PCR instrument is preheated, and then the reaction tube is quickly transferred from the ice to the PCR instrument).

TABLE 4

| Repair reagents | |
|---|---|
| Zymo Research, 5-Methylcytosine dNTP Mix (10 mM) | 0.75 μl |
| Thermopol ® Reaction Buffer (10×) | 0.75 μl |
| Sulfolobus DNA Polymerase IV | 0.5 μl |

(7) Bisulfite treatment: Non-methylated C was converted into U by a bisulfite, while methylated C remained the original methylation state. The reagents in Table 5 were added sequentially to the PCR tube, and a resulting mixture was thoroughly mixed and placed in a PCR instrument.

TABLE 5

| Reagents used for the bisulfite treatment | |
|---|---|
| ARF35 (Carrier DNA, 1 μg/μl) | 1 μl |
| Nuclease-Free Water | 19 μl |
| Bisulfite Solution | 85 μl |
| Protect buffer | 15 μl |

Reaction conditions were: 95° C. for 5 min, 60° C. for 10 min, 95° C. for 5 min, and 60° C. for 20 min (the hot cap temperature was required at 105° C.); after the reaction was completed, a solution in a PCR tube was completely transferred to a 1.5 mL EP tube; according to a number of experimental samples, fresh BL buffer+Carrier RNA was prepared according to the table below, 310 μL of the freshly-prepared BL buffer+carrier RNA was added to the EP tube with the solution, and 250 μl of 100% ethanol (stored at −20° C.) was added to the EP tube; the EP tube was shaken on a shaker for 15 s (a hand was placed on a shaker for 3 seconds, 5 times in total), a resulting solution in the EP tube was completely transferred to a chromatography column with a collection tube sleeved, and the chromatography column was centrifuged in a centrifuge at 25° C. and 13,300 rpm for 1 min; a liquid collected in the collection tube was discarded, the chromatography column was sleeved back in the collection tube, 500 μL of a BW buffer was added to the chromatography column, and the chromatography column was centrifuged in a centrifuge at 25° C. and 13,300 rpm for 1 min; a liquid collected in the collection tube was discarded, the chromatography column was sleeved back in the collection tube, 500 μL of a BD buffer was added to the chromatography column, and the chromatography column was incubated at room temperature for 15 min and then centrifuged in a centrifuge at 25° C. and 13,300 rpm for 1 min; a liquid collected in the collection tube was discarded, the chromatography column was sleeved back in the collection tube, 500 μL of a BW buffer was added to the chromatography column, and the chromatography column was centrifuged in a centrifuge at 25° C. and 13,300 rpm for 1 min (this step was repeated twice); 250 μL of 100% ethanol (stored at −20° C.) was added to the chromatography column, and the chromatography column was centrifuged in a centrifuge at 25° C. and 13,300 rpm for 1 min; the chromatography column was sleeved in a new collection tube, the chromatography column was centrifuged in a centrifuge at 25° C. and 13,300 rpm for 1 min to remove the residual solution, and after the centrifugation was completed, the chromatography column was then sleeved in a new EP tube; 17 μL of Nuclease-Free Water pre-heated to 60° C. was added to a middle of a membrane of the chromatography column, the EP tube was gently capped, and the chromatography column was incubated at room temperature for 1 min and then centrifuged in a centrifuge at 25° C. and 13,300 rpm for 1 min to elute DNA (this step was repeated twice).

BL buffer+carrier RNA was prepared as shown in Table 6.

TABLE 6

| Preparation of BL buffer + carrier RNA | | | | | | | | |
|---|---|---|---|---|---|---|---|---|
| | Number of samples | | | | | | | |
| | 1 | 2 | 4 | 8 | 16 | 18 | 24 | 48 |
| BL buffer (μl) | 350 | 700 | 1400 | 2800 | 5600 | 6300 | 8400 | 16800 |
| Carrier RNA (μl) | 3.5 | 7 | 14 | 28 | 56 | 63 | 84 | 168 |

(8) A first round of PCR amplification of DNA fragments: Fragments of single-cell gDNA were amplified, and a DNA concentration was increased to a nanogram (ng) level. All DNA samples eluted in the previous step were transferred to a new PCR tube, the reagents in Table 7 were added sequentially to the PCR tube, and a resulting mixture was thoroughly mixed and then placed in a PCR instrument to allow a reaction under the following conditions: 95° C. for 5 min (1 cycle), 95° C. for 30 s, 56° C. for 30 s, 72° C. for 45 s (27 cycles), and 72° C. for 10 min (1 cycle) (the hot cap temperature was required at 105° C.); and after the reaction was completed, DNA was purified, and the excess primers were removed, where if the purification was conducted with a Zymo reagent, purification steps were as follows: a solution (about 50 μL) in the PCR tube was transferred to a new EP tube, 8 times volume of the solution, i.e., 400 μL of a DNA Binding Buffer (DNA Clean & Concentrator-5), was added to the EP tube (400 μL of the buffer: 50 μL of the sample), a resulting mixture was thoroughly mixed, and then 450 μL of a resulting solution in the EP tube was transferred to a chromatography column with a collection tube sleeved; the chromatography column was centrifuged in a centrifuge at 25° C. and 10,000 rpm for 30 s, and a resulting filtrate was discarded; the chromatography column was sleeved back in the collection tube, 200 μL of a Wash buffer was added to the chromatography column, the chromatography column was centrifuged in a centrifuge at 25° C. and 10,000 rpm for 30 s, and a resulting filtrate was discarded (this step was repeated twice); the chromatography column was sleeved in a new EP tube, 9 μL of Nuclease-Free Water pre-heated to 60° C. was added to the chromatography column, and the chromatography column was incubated for 1 min and then centrifuged in a centrifuge at 25° C. and 10,000 rpm for 1 min; and after the centrifugation was completed, 9.5 μL of Nuclease-Free Water pre-heated to 60° C. was added directly to the chromatography column, and the chromatography column was incubated for 1 min and then centrifuged in a centrifuge at 25° C. and 10,000 rpm for 1 min to elute DNA.

TABLE 7

| System for the first round of PCR amplification | |
|---|---|
| $MgCl_2$ (25 mM) | 5 μl |
| 10× Takara Taq PCR buffer ($Mg^{2+}$ Free) | 5 μl |
| TaKaRa Epi Taq HS (5 U/μl) | 0.5 μl |

TABLE 7-continued

| System for the first round of PCR amplification | |
|---|---|
| dNTP (2.5 mM) | 2 μl |
| Primer: J10P4 (10 μM) | 5 μl |

(9) Removal of an adapter through BciVI cleavage after the first round of amplification and retaining of a barcode: Primers at termini of a DNA fragment after PCR amplification were removed. The reagents in Table 8 were added sequentially to the PCR tube, and a resulting mixture was thoroughly mixed and placed in a PCR instrument, and reaction conditions were: 37° C. for 2 h and 65° C. for 20 min (the hot cap temperature was at 50° C.); and after the reaction was completed, DNA was purified by the method in step 8.

TABLE 8

| System for enzyme cleavage | |
|---|---|
| BciVI | 1 μl |
| 10× CutSmart Buffer | 2 μl |

(10) Ligation of an NGS adapter: The reagents in Table 9 were added sequentially to the PCR tube, and an NGS adapter sequence was ligated. Operations and conditions for the ligation refer to step 4, and a DNA purification method refers to step 8.

TABLE 9

| Reagents used for the ligation of the NGS adapter | |
|---|---|
| Nuclease-Free Water | 1 μl |
| PJad12, 50 μM | 2.5 μl |
| ATP, 10 mM | 2.5 μl |
| 10× Fast Link Ligation Buffer | 3 μl |
| Fast-Link ™ DNA ligation Kit | 1 μl |

(11) Electrophoresis separation, and purification and recovery of a target fragment with a gel: DNA fragments were of different sizes and diffused; and a target fragment may be recovered through running of gels, and a DNA concentration may be preliminarily determined based on a brightness of a band. A 2% precast gel was taken and arranged on an electrophoresis instrument, 16 μL of Nuclease-Free Water and 4 μL of 50 bp Maker were added to two Maker wells, respectively, and 20 μL of a sample was added to a sample well; the electrophoresis instrument was started, and when the 50 bp Maker ran to the bottommost position, electrophoresis was finished (about 18 min to 21 min); bands were observed and photographed on a gel imaging system, 125 bp to 300 bp was recovered and placed in a new EP tube, and the EP tube was marked and stored in a 4° C. refrigerator; a weight of each recovered gel was measured by an electronic balance; an ADB solution was added to the EP tube with 0.1 g of a gel per 300 μL of ADB, and the EP tube was placed in a 55° C. metal bath to allow dissolution for 10 min to 15 min; a resulting solution in the EP tube was transferred to a chromatography column with a collection tube sleeved, the chromatography column was centrifuged in a centrifuge at 25° C. and 10,000 rpm for 30 s, and a resulting filtrate was discarded; the chromatography column was sleeved back in the collection tube, 200 μL of a Wash buffer was added to the chromatography column, the chromatography column was centrifuged in a centrifuge at 25° C. and 10,000 rpm for 30 s, and a resulting filtrate was discarded (this step was repeated twice); the chromatography column was sleeved in a new EP tube, 10 μL of Nuclease-Free Water pre-heated to 60° C. was added to the chromatography column, and the chromatography column was incubated for 1 min and centrifuged in a centrifuge at 25° C. and 10,000 rpm for 1 min; and after the centrifugation was completed, 15 μL of Nuclease-Free Water pre-heated to 60° C. was added to the chromatography column, and the chromatography column was incubated for 1 min and centrifuged in a centrifuge at 25° C. and 10,000 rpm for 1 min to elute DNA. A DNA concentration was determined by Qubit 3.0.

(12) A second round of PCR amplification for DNA fragments including sample indexes: The reagents in Table 10 were added sequentially to a PCR tube, an index required for sequencing was ligated, and DNA fragments ligated with indexes were amplified. 5 ng of the DNA sample eluted in the previous step was taken and added to a new PCR tube, and a resulting mixture was thoroughly mixed and placed in a PCR instrument, and the reaction conditions were: 95° C. for 1 min (1 cycle), 95° C. for 30 s, 57° C. for 30 s, 72° C. for 45 s (7 to 8 cycles), and 72° C. for 10 min (1 cycle) (the hot cap temperature was required at 105° C.); and after the reaction was completed, DNA was purified by the method in step 8.

TABLE 10

| System for the second round of PCR amplification | |
|---|---|
| DNA sample eluted in the previous step | X μl (5 ng) |
| Nuclease-Free Water | Y μl |
| GC-rich Phusion High-Fidelity 2× Master Mix | 12.5 μl |
| VPE11a (25 μM) | 1 μl |
| Index (25 μM) | 1 μl |
| Total | 25 μl |

(13) Purification and recovery of target DNA fragments via running of gels: reference to step (11) (note: the DNA fragments recovered in this step have a size of 175 bp to 350 bp).

(14) Quality control and sequencing: A DNA concentration was detected by Qubit 3.0, the concentration was about 3 ng/μL, and 12 μL was required. A Hiseq X Ten platform of Illumina was adopted for sequencing.

Figure 9:
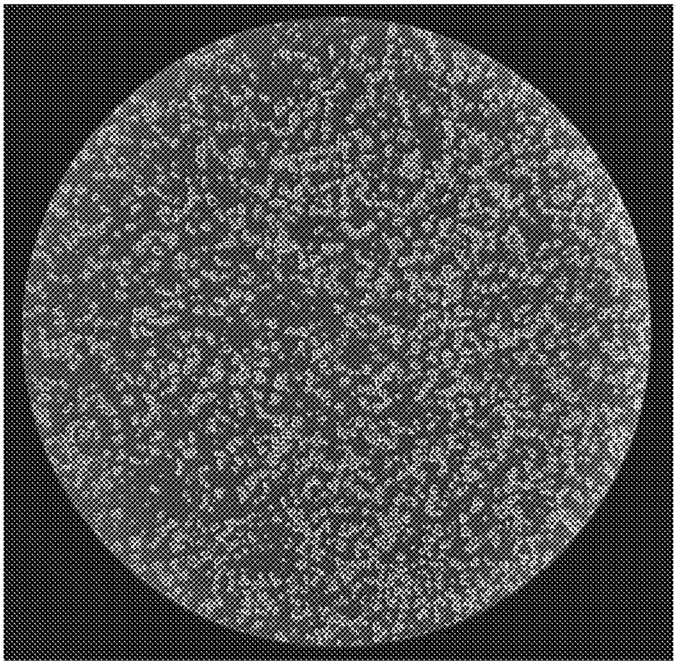
FIG. 9 is an image of K562 cells.

Experimental results obtained with K562 cells (an image of the cells under a microscope was shown in FIG. 9) and the experimental method above in the present application were shown in FIG. 10A to FIG. 17.

It can be seen from FIG. 10A to FIG. 10D that the fragments recovered in the first round have a length of 125 bp to 300 bp, and the fragments recovered in the second round have a length of 175 bp to 350 bp (a fragment length range of the final library).

Figure 11:
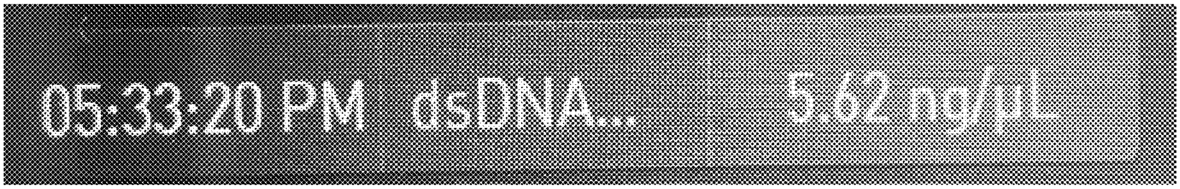
FIG. 11 is a detection result graph of a library concentration by a Qubit 3.0 fluorometer after pooling of library construction for 16 single cells of a cell line K562.

The results in FIG. 11 show that a final library concentration is 5.62 ng/pt.

Figure 10A:
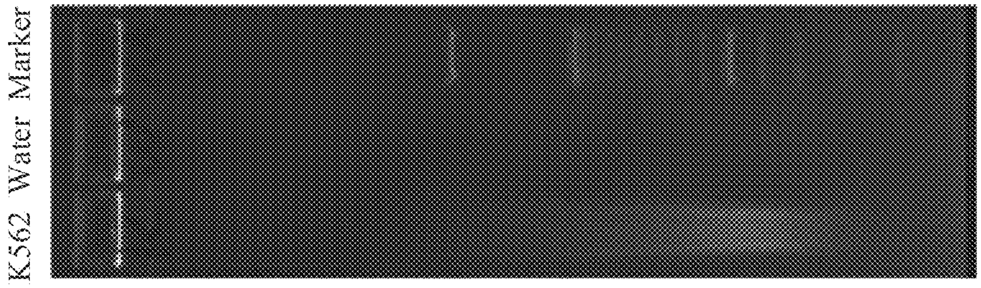
Figure 10B:
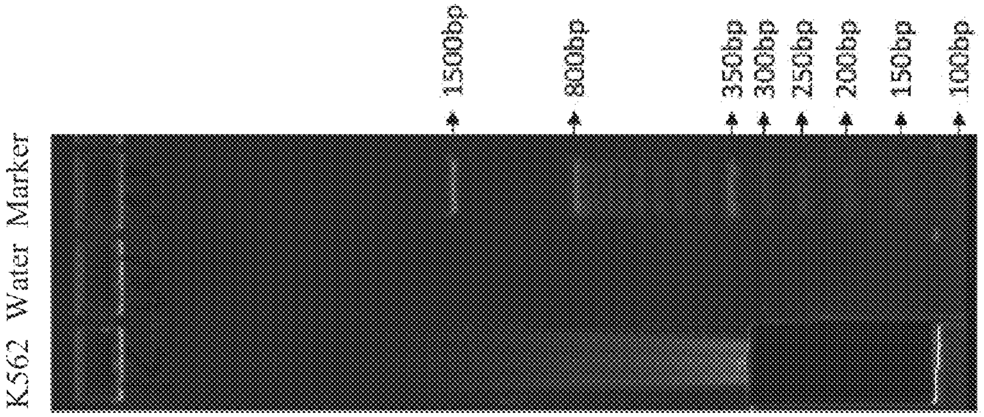
Figure 10C:
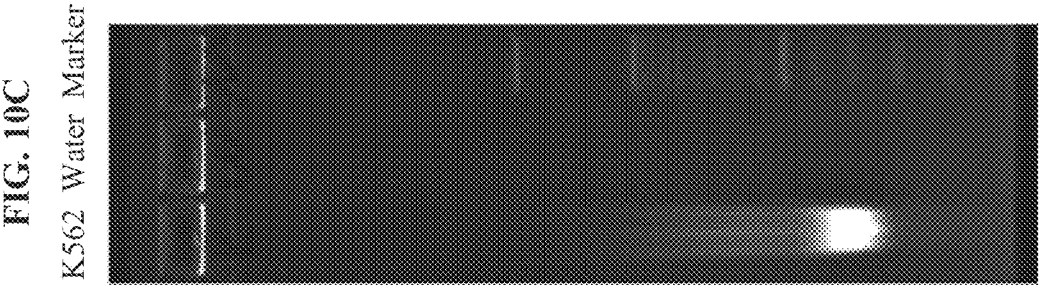
Figure 10D:
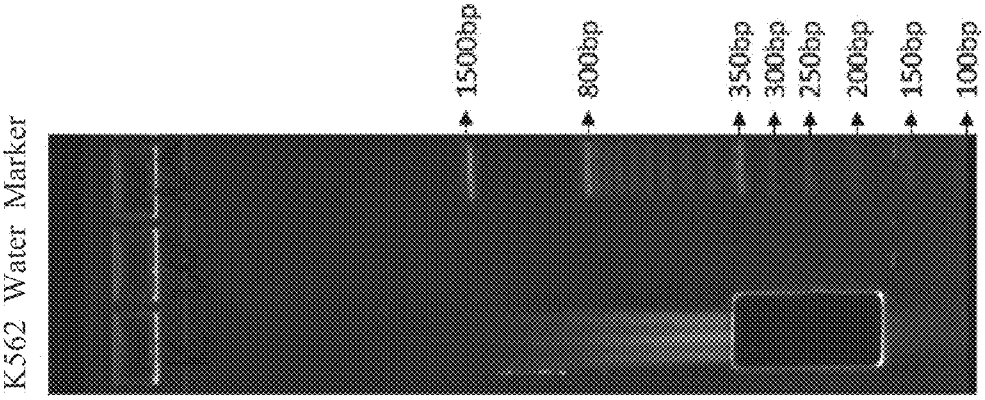
Figure 12:
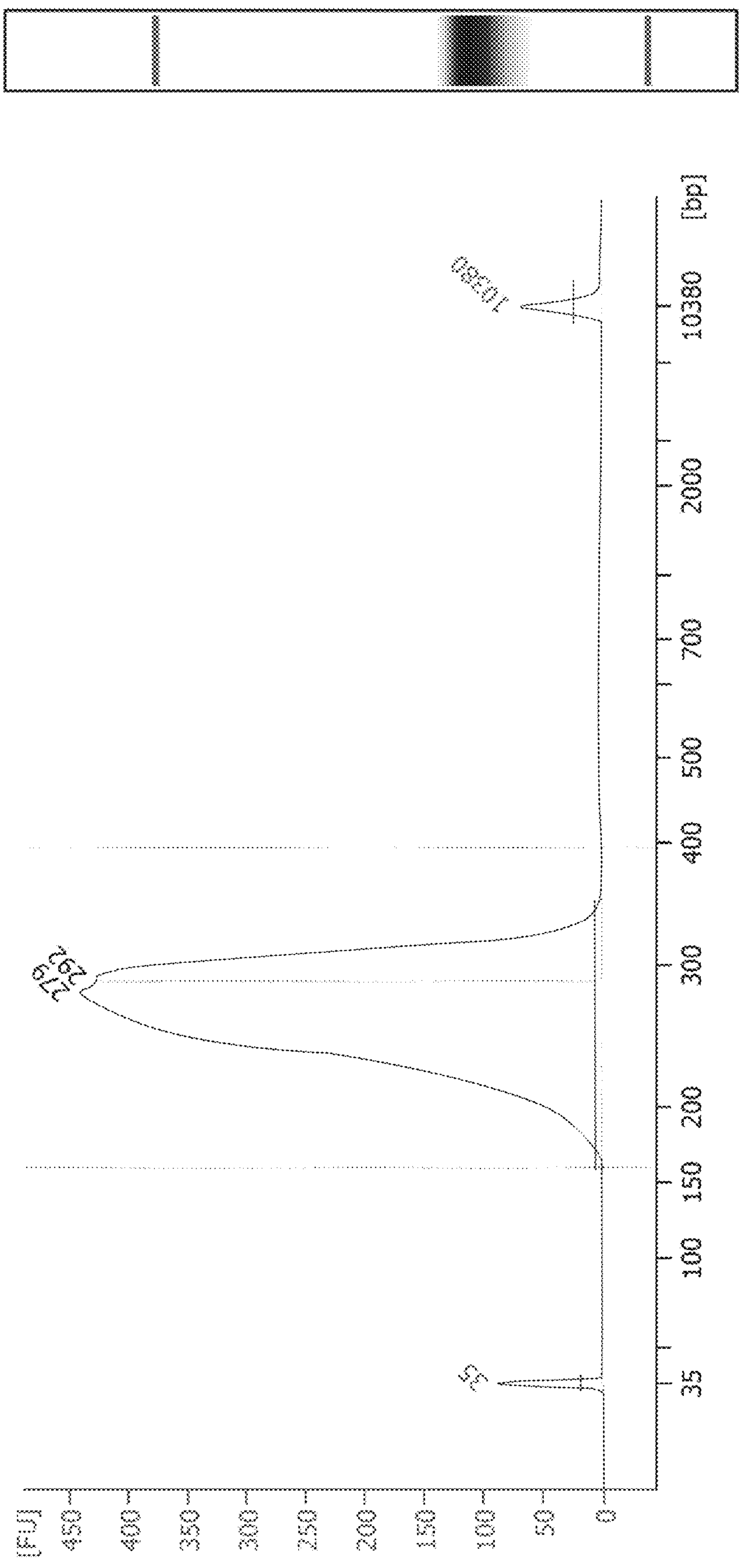
FIG. 12 is a graph of fragment distribution acquired by a Agilent 2100 bioanalyzer after pooling of library construction for 16 single cells of a cell line K562, which has been smoothed.

The results in FIG. 12 show that the results obtained by the Agilent 2100 bioanalyzer are consistent with a range of fragments recovered from E-Gel in FIG. 10D, a main peak is at 279 bp, and a peak pattern is in line with an expectation.

Figure 13:
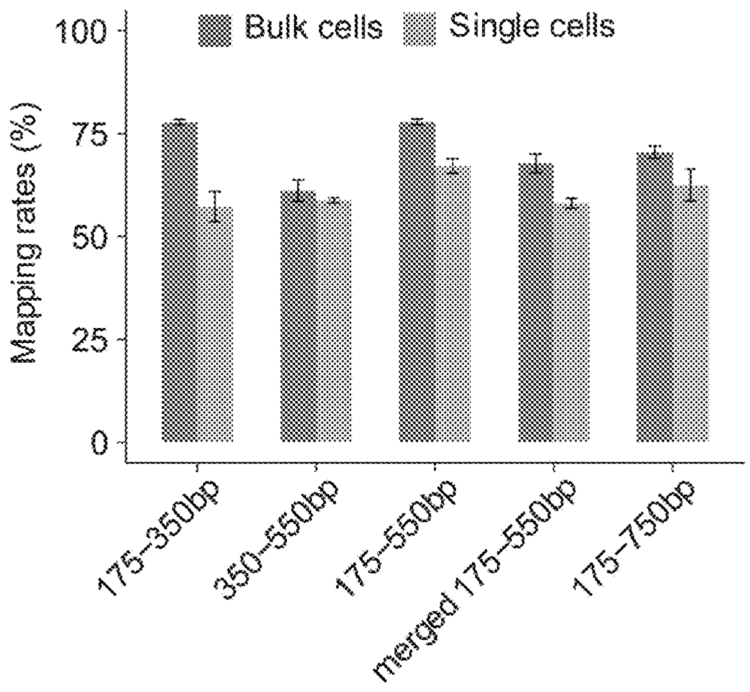
FIG. 13 is a graph of mapping rates of methylation libraries for single cells and a micro-bulk of cells of a cell line K562 in different recovered fragment ranges obtained through RStudio analysis.

The results in FIG. 13 show that average mapping rates of methylation libraries for K562 single cells and a micro-bulk of cells in different ranges of recovered fragments all are 55% or higher, indicating that the method of the present application has strong robustness.

Figure 14:
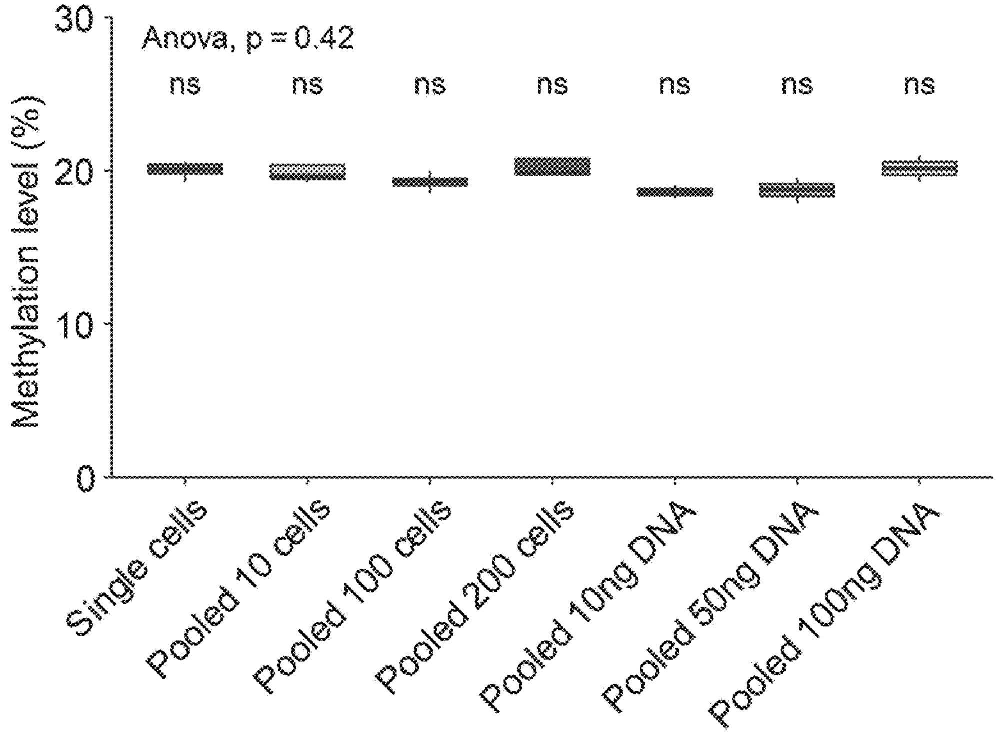
FIG. 14 is a graph of methylation levels at CpG sites in single cells, a micro-bulk of cells, and extracted DNA samples of a cell line K562 through RStudio analysis.
Figure 15A:
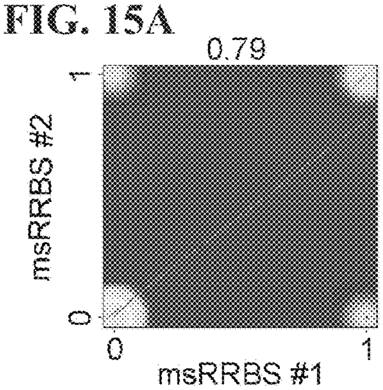
FIG. 15A-FIG. 15F are graphs of correlation of methylation profiles based on CpG sites between K562 single cells (FIG. 15A), single cells and a micro-bulk of cells (FIG. 15B), merged single cells and a micro-bulk of cells (FIG. 15C), a micro-bulk of cells (FIG. 15D), a micro-bulk of cells and methylation EPIC chips (FIG. 15E), and a micro-bulk of cells and WGBS (FIG. 15F) through RStudio analysis.
Figure 15B:
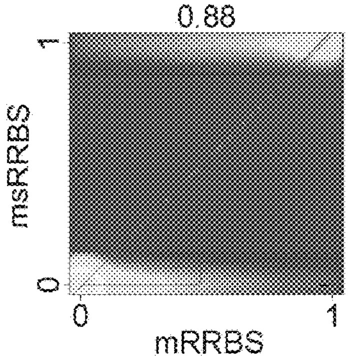
Figure 15C:
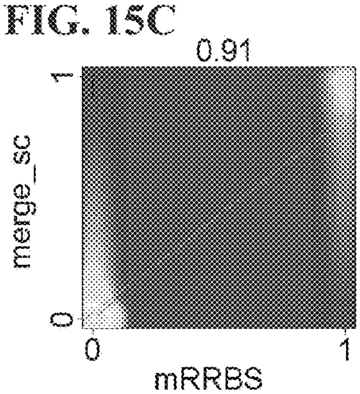
Figure 15D:
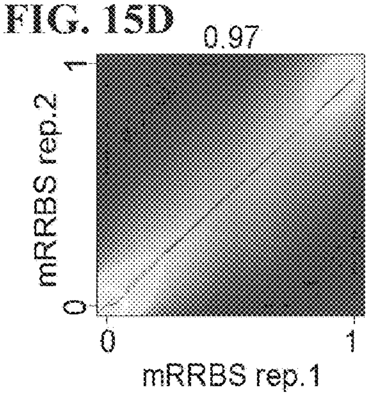
Figure 15E:
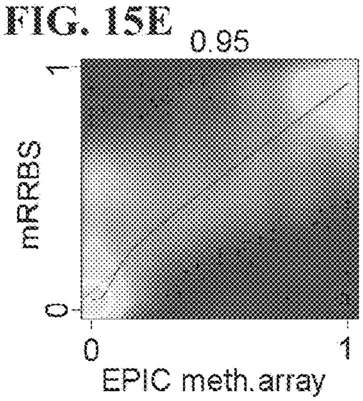
Figure 15F:
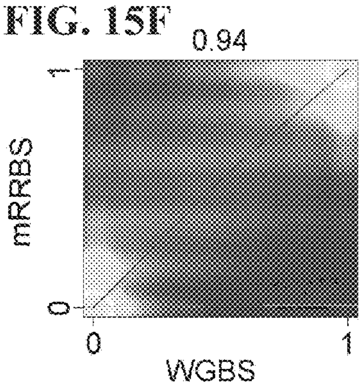

The results in FIG. 14 show that there is no significant difference among methylation levels at CpG sites in single cells, a micro-bulk of cells, and extracted DNA samples of a K562 cell line, indicating the reliability of the method of the present application.

The results of FIG. 15A to FIG. 15F show that a correlation between K562 single cells is 0.79 (FIG. 15A), a correlation between single cells and a micro-bulk of cells is 0.88 (FIG. 15B), a correlation between merged single cells and a micro-bulk of cells is 0.91 (FIG. 15C), a correlation between a micro-bulk of cells is 0.97 (FIG. 15D), a correlation between a micro-bulk of cells and methylation EPIC chips is 0.95 (FIG. 15E), and a correlation between a micro-bulk of cells and WGBS is 0.94 (FIG. 15F), indicating the high reliability of the method of the present application.

Figure 16:
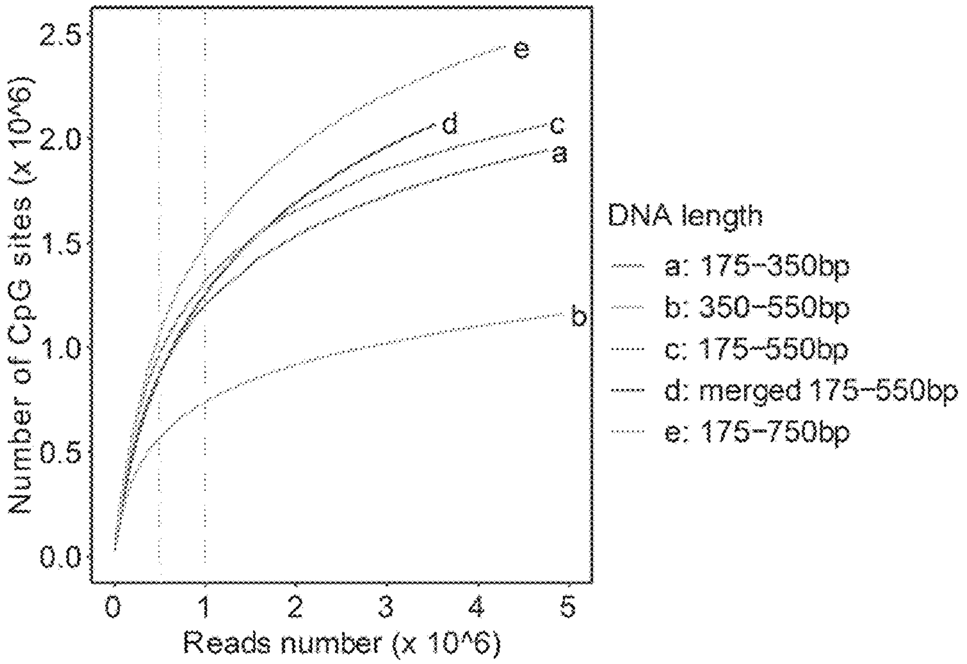
FIG. 16 is a graph of sequencing saturation analysis results of single cells in a methylation library of a cell line K562 through RStudio analysis, where saturation curves of CpG sites in single cells detected under different reads are calculated separately.

FIG. 16 shows saturation analysis results of methylation libraries for K562 single cells in different ranges of recovered fragments, and 1.25 millions of CpG sites are obtained with 1 million of readings, that is, the method of the present application may acquire information of a large number of CpG sites with a small number of sequencing readings, thereby reducing a cost of sequencing.

Figure 17:
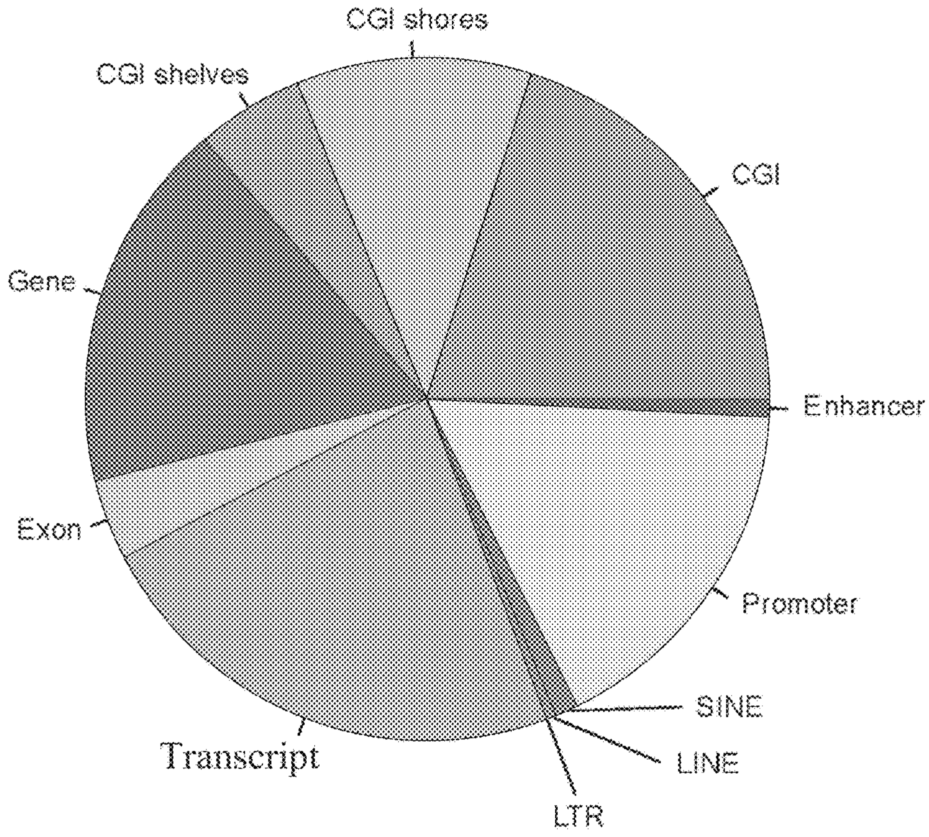
FIG. 17 is a graph of distribution results of reads of single-cell barcodes of 20 samples in a methylation library of a cell line K562 compared with different regions of a genome through RStudio analysis, where CGI: CpG island, SINE: short interspersed nuclear element, LINE: long interspersed nuclear element, and LTR: long terminal repeat; and due to the intersection of CpG sites between various functional elements, in this figure, each functional element is calculated independently to obtain a detection rate of the functional element, and then, with a detection rate of the 11 functional elements in the figure as 100%, a proportion of each functional element among the detected functional elements is obtained.

The results in FIG. 17 show that the method of the present application may determine proportions of functional elements, among which the proportions of CGIs, promoters, genes, and transcripts are relatively high; at the same time, these results corroborate that most of the functional elements detected by the method of the present application are CGIs and promoters.

The present application includes novel barcode adapters and primers, corresponding supporting experimental reagents and/or instruments, experimental procedures, and data analysis procedures.

(1) The short adapter (barcode adapter) used in the present application is produced through a special treatment of a long oligonucleotide (shown in SEQ ID NO: 1) and a short oligonucleotide (shown in SEQ ID NO: 2) (as shown in FIG. 4). Neither of the two oligonucleotides oligo requires a phosphorylated 5' end, but the 3' end of the short oligonucleotide needs to be modified by adding a blocking group. A specific preparation process of a barcode adapter was: ① SEQ ID NO: 1 and SEQ ID NO: 2 each were dissolved with a 1×TE buffer to obtain oligonucleotide solutions with concentrations of 2 nmol/μL and 0.5 nmol/μL, respectively (the 1×TE buffer includes components such as 10 mM Tris-HCl and 1 mM EDTA, and may provide an environment of a low-salt buffer for the sequences). ② 2 μL of 10× T4 DNA ligation buffer, the oligo1 and oligo2 solutions, and 10 μL of Nuclease-Free Water were added to a reaction system, then the reaction system was sealed, and placed in 94° C. water bath for 3 min, then quickly cooled to 80° C., and then naturally cooled to room temperature. ③ Finally, 20 μL of Nuclease-Free Water was added to a resulting reaction solution, and a final concentration was 0.05 nmol/μL, and when used finally, the reaction solution was diluted with Nuclease-Free Water to 0.01 nmol/μL. After being treated by this method, SEQ ID NO: 1 and SEQ ID NO: 2 may form a short adapter in which partial bases are complementarily paired.

Figure 1:
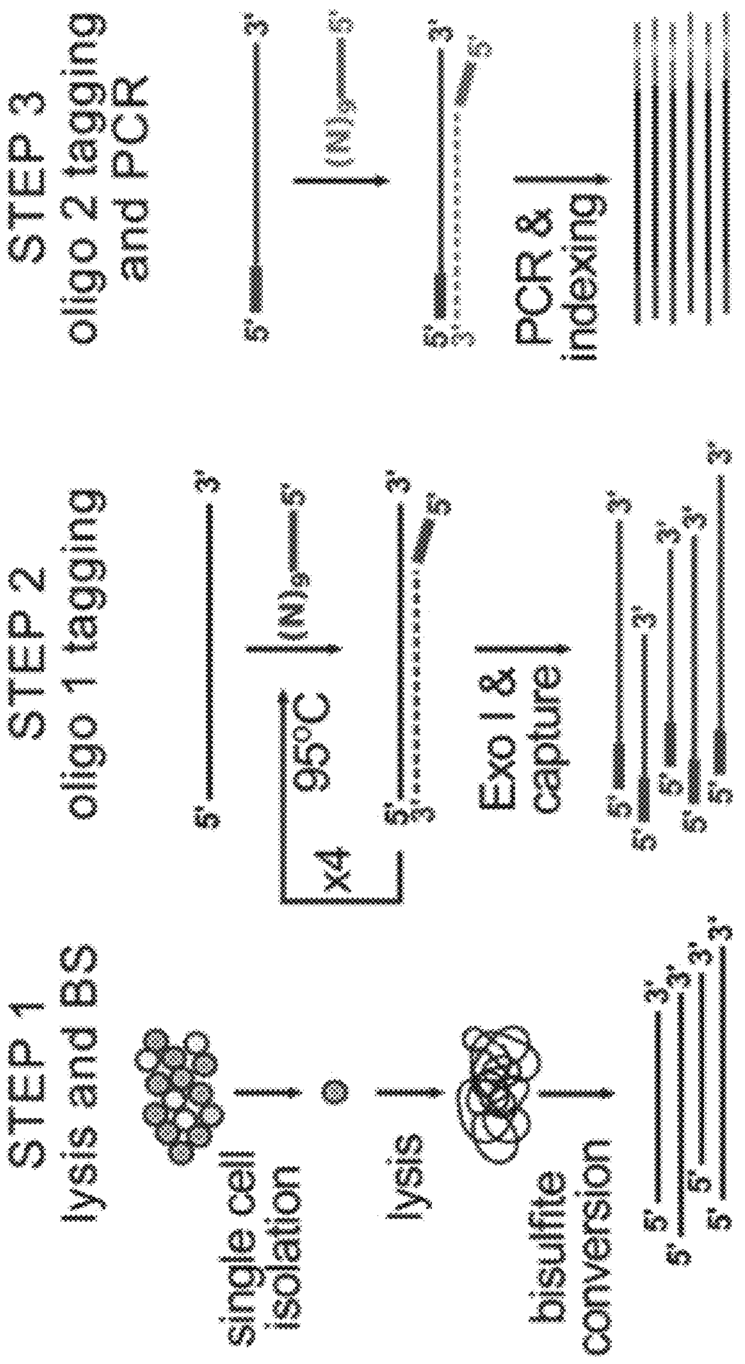
FIG. 1 PRIOR ART
FIG. 1 shows a library construction process of scBS (or scWGBS) and a coverage degree of CpG sites.
Figure 2:
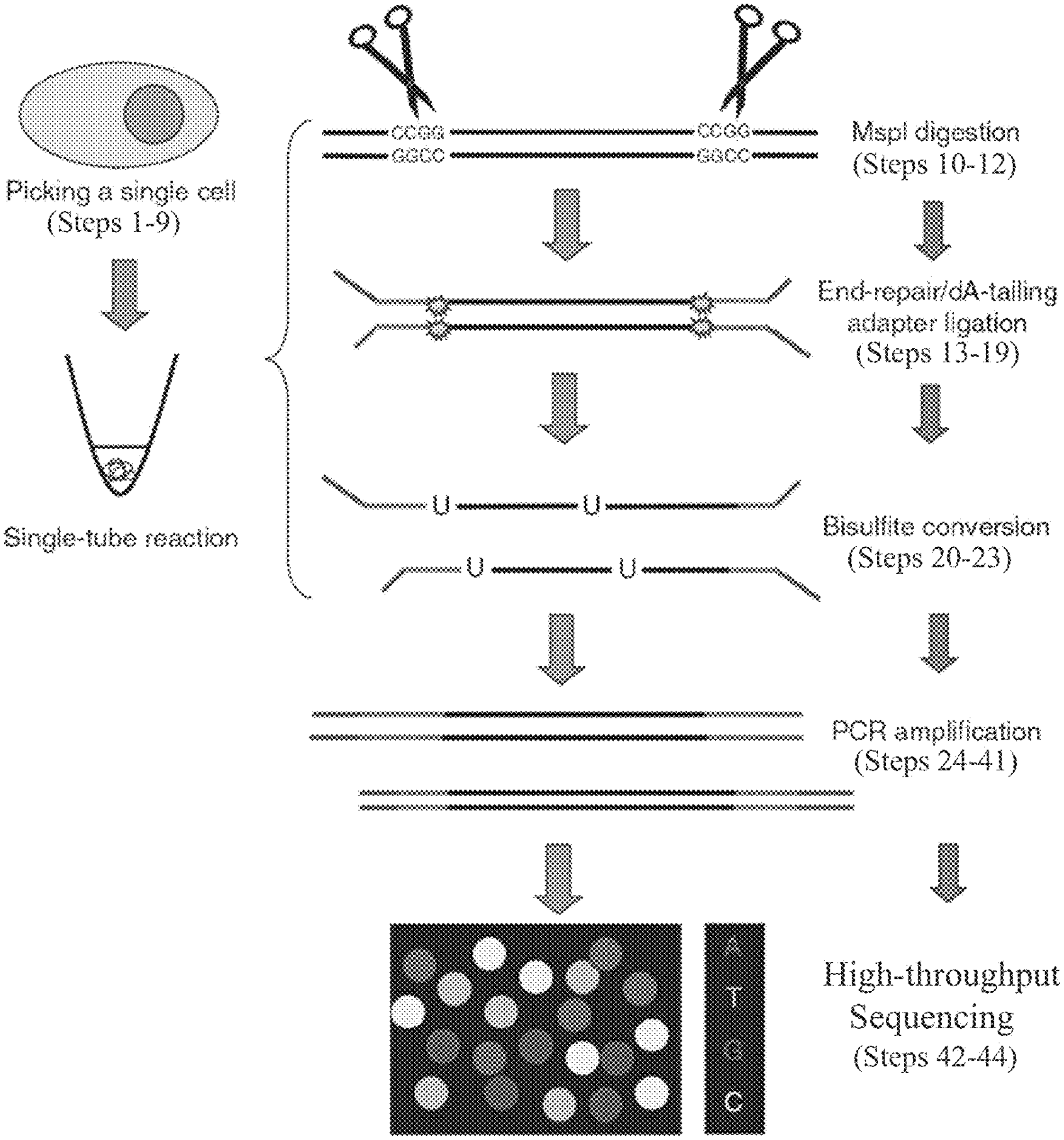
FIG. 2 PRIOR ART
FIG. 2 shows a library construction process of scRRBS.
Figure 3:
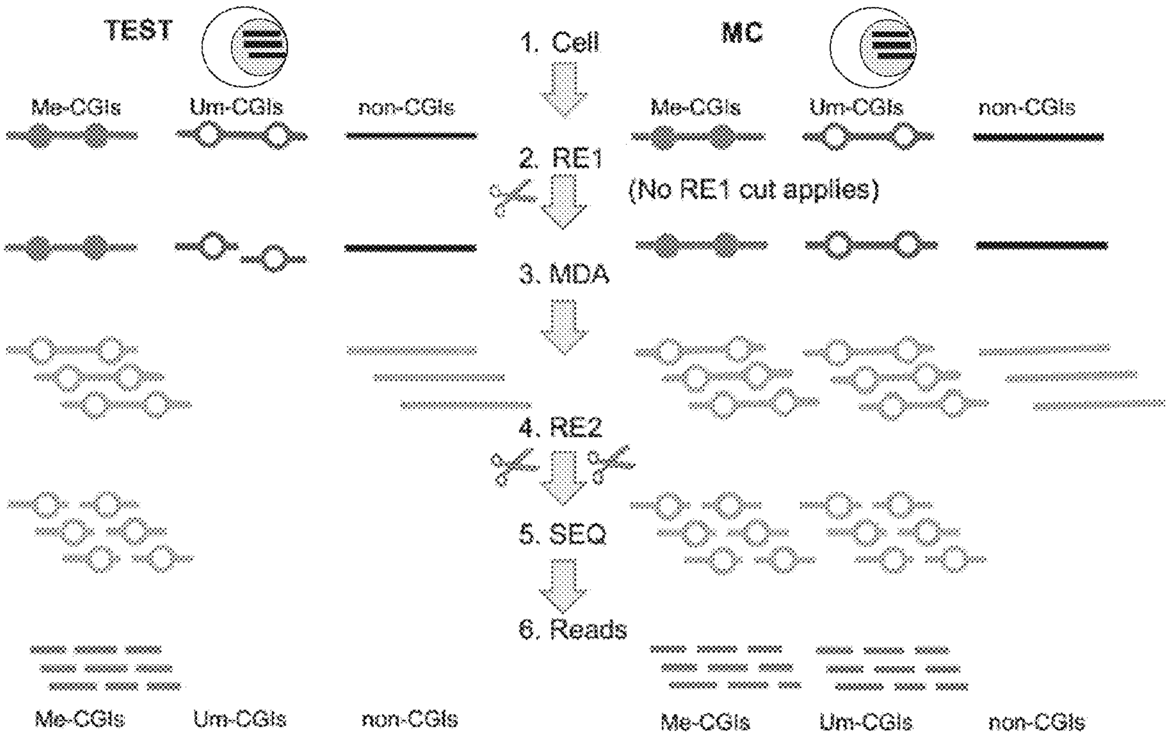
FIG. 3 PRIOR ART
FIG. 3 shows a library construction process of a scCGI-seq technology.
Figure 5:
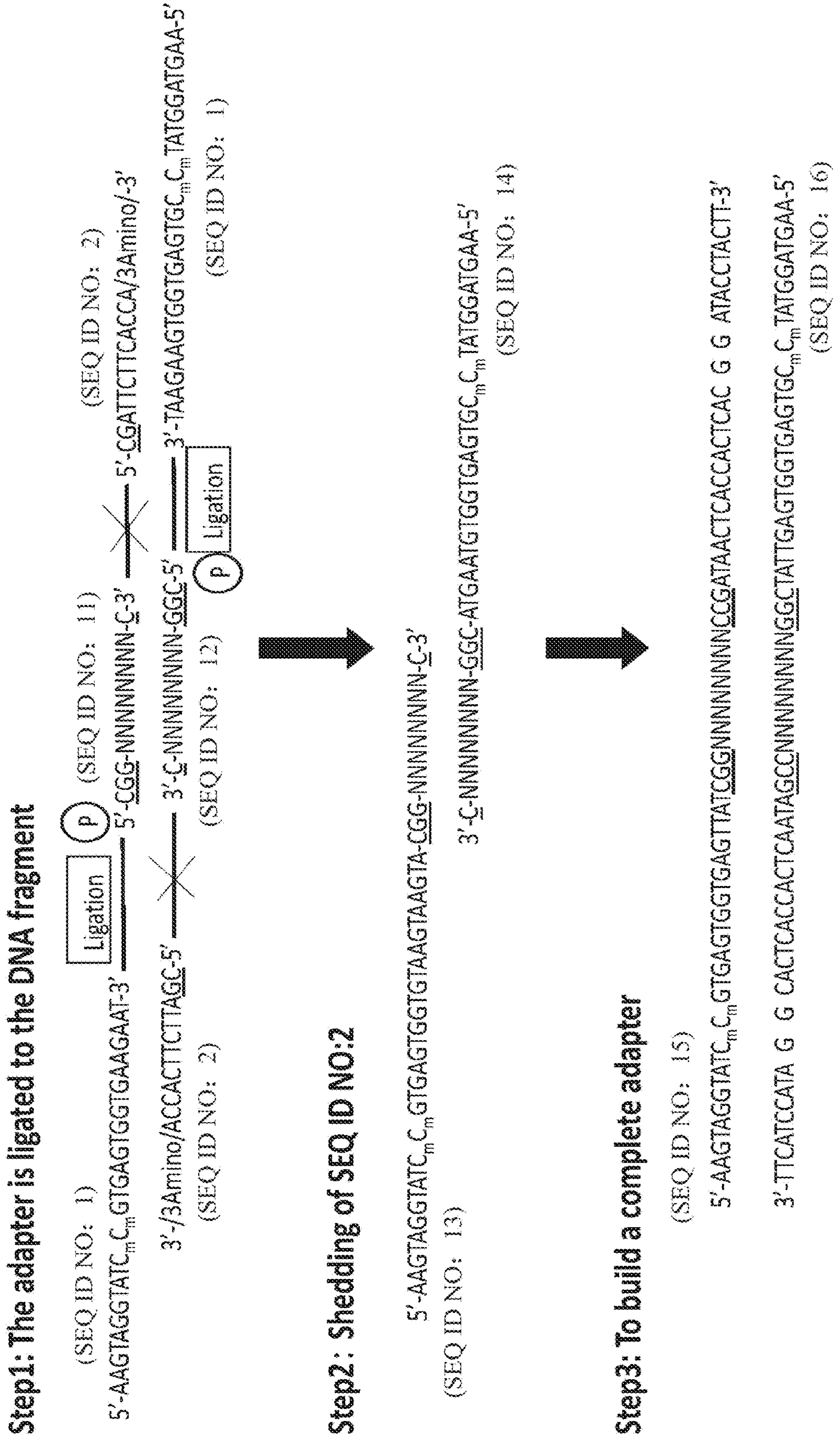
FIG. 5 shows the ligation and construction of a barcode adapter, where "3Amino" indicates that the 3' end of the oligonucleotide is modified by amino; "N" represents any base selected from the group consisting of A, T, C, and G; "P" in a circle indicates a phosphorylation modification; "Cm" represents C modified by methylation; "x" on a horizontal line indicates a non-chemical bond ligation; and the underlined base indicates a site at which a barcode adapter is ligated to a target DNA fragment; where a sequence corresponding to SEQ ID NO: 11 is 5'-CGG-NNNNNNNNC, and a sequence corresponding to SEQ ID NO: 12 is 5'-CGGNNNNNNNNC, and the "NNNNNNNN" in the middle of the two are complementarily paired with each other; a sequence corresponding to SEQ ID NO: 13 is 5'-AAGTAGGTATCmCmGT-GAGTGGTGTAAGTAAGTA-CGG-NNNNNNNN-C-3'; a sequence corresponding to SEQ ID NO: 14 is 5'-AAGTAGGTATCmCmGT-GAGTGGTGTAAGTAAGTA-CGG-NNNNNNNN-C-3'; a sequence corresponding to SEQ ID NO: 15 is 5'-AAGTAGGTATCmCmGTGAGTGGTGAGTTATCGG-NNNNNNNNCCGATAACTCACCA CTCACGGATACC-TACTT-3'; a sequence corresponding to SEQ ID NO: 16 is 5'-AAGTAGGTATCmCmGTGAGTGGTGAGTTATCGG-NNNNNNNNCCGATAACTCACCA CTCACGGATACC-TACTT-3'; wherein the sequences shown in SEQ ID NO: 11 and SEQ ID NO: 12 are different in most cases and the same in a very few cases, which is also applicable to the sequences shown in SEQ ID NO: 13 and SEQ ID NO: 14 and the sequences shown in SEQ ID NO: 15 and SEQ ID NO: 16.

(2) In the present application, before a barcode adapter is ligated, it is not necessary to fill an end of a DNA fragment, and it is also not necessary to add A to an end (because the efficiency of end-filling and A addition is low, it is easy to cause failed addition of A to some DNA fragments, thereby resulting in failed ligation of an adapter and a loss of DNA; and at a pg-quantity DNA level of a single cell, additional enzymatic operations will increase a chance of DNA damage, and it is difficult to allow high consistency among different samples); and under an action of a ligase, SEQ ID NO: 1 in the short adapter may be ligated to the 5' end of a DNA fragment (the 5' end of the DNA fragment is phosphorylated), but SEQ ID NO: 2 (its 5' end is not phosphorylated) may not be ligated to the 3' end of the DNA fragment, and at an appropriate high temperature, SEQ ID NO: 2 will be separated. Under reaction conditions such as polymerase *Sulfolobus* DNA polymerase IV and dNTPs (including methylated dmCTP), when a temperature reaches 55° C., SEQ ID NO: 1 ligated to the DNA fragment will synthesize a complementary strand, thus constructing a complete adapter. The polymerase *Sulfolobus* DNA polymerase IV is characterized by template-dependence, optimal activity at a high temperature (avoiding renaturation of SEQ ID NO: 1 and SEQ ID NO: 2 at 55° C.), and no activity of strand displacement (as a result, the synthesis of a new DNA strand will not occur in the case of long DNA with a nick; and the latter has the disadvantage of causing an artificial methylation state) (as shown in FIG. 5).

(3) In the present application, a large number of different barcode sequences may be designed, such as tens, hundreds, thousands, or even tens of thousands of different barcode sequences; and with one barcode for tagging a single cell, a large number of single cells may be tagged. As a result, in the technical solution used in the present application, different single cells are tagged with different barcodes, and then these tagged single cells are pooled in a reaction system for library construction, which improves the experimental efficiency, reduces the experimental cost, and allows the consistency of experimental operations. In the existing technical solutions, the early tagging of single cells with barcodes is not provided, but after bisulfite conversion is conducted independently for each cell, PCR is conducted independently, and different indexes are added for each cell, different single-cell samples may be pooled in one tube to acquire single-cell information. If a library is constructed simultaneously for 96 single cells in a same reaction system without a tagging treatment, then it is not called library construction of single-cell methylation, but library construction of small quantity of a micro-bulk of cells, and finally, it is impossible to classify the methylation of each single cell.

Key points of a design scheme of a novel barcode adapter: (1) The barcode adapter may be directly ligated to a DNA fragment obtained after enzyme cleavage, and it is not necessary to conduct enzymatic filling or cleavage for a DNA fragment and add A to the 3' end, which reduces the loss of DNA and simplifies the operations of a single cell. (2) The short adapter is capable of reducing a chance of DNA breakage during methylation conversion, thereby reducing the loss of target DNA fragments and increasing the coverage degree. (3) The ligation of a cell-specific barcode adapter enables the early pooling of samples, such that downstream operations (bisulfite treatment, PCR, gel electrophoresis recovery, length selection of target DNA, and the like) may be conducted in a single test tube, which simplifies the independent operations of a large number of single cells into similar population cell operations of a sample without losing the independent tagging of different cells. (4) The operation simplification does not affect the second round of amplification, and an index is added to different samples. We (and perhaps peers) have tried to ligate a conventional NGS adapter to single-cell DNA fragments after enzyme cleavage, but operations should be conducted independently for each cell until PCR amplification is completed, which leads to large time and reagent consumption, low coverage degree, and inconsistency. We have also designed a conventional double-stranded adapter that may be directly ligated to complementary termini of DNA, but stable adapter dimers are very easily produced and super-abundantly amplified during a subsequent PCR process, which completely blocks the amplification of target DNA. In the present application, this step (ligation of a conventional adapter) is merely a sample-specific tagging operation for a large number of single cells from a same batch of samples.

Optimized designs of this experiment are provided as complements to the adapter above, such as two-step amplification; staged recovery based on DNA fragment sizes; and use of a specially designed carrier for DNA fragment attachments (or shield) and the like to resist the damage of methylation conversion to target DNA, etc.

Figure 6:
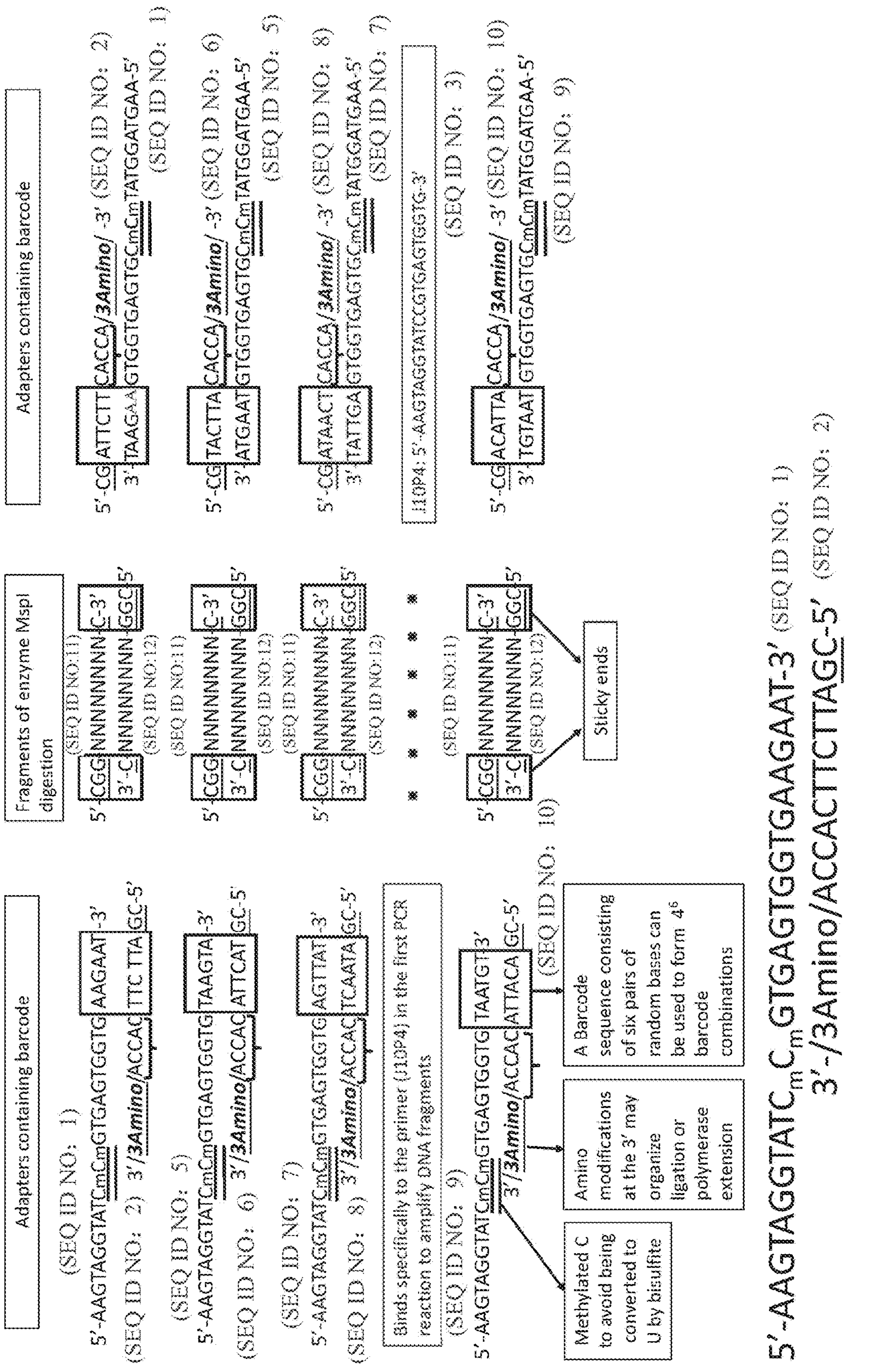
FIG. 6 is a schematic diagram of a part of the method of the present application, consisting of three sequence blocks: left (adapters containing barcode), middle (fragments of enzyme MspI digestion), and right (adapters containing barcode), where sequences on the right are exactly the same as a long oligonucleotide sequence and a short oligonucleotide sequence in a same row on the left; sequences in the first row on the left are as follows: a long oligonucleotide sequence: 5'-AAGTAGGTATCmCmGTGAGTGGTG AAGAAT-3' (SEQ ID NO: 1) and a short oligonucleotide sequence: 5'-CG ATTCTT CACCA/3Amino/-3' (SEQ ID NO: 2); sequences in the second row on the left are as follows: a long oligonucleotide sequence: 5'-AAGTAGGTATCmCmGTGAGTGGTGTAAGTA-3' (SEQ ID NO: 5) and a short oligonucleotide sequence: 5'-CG TACTTA CACCA/3Amino/-3' (SEQ ID NO: 6); sequences in the third row on the left are as follows: a long oligonucleotide sequence: 5'-AAGTAGGTATCmCmGT-GAGTGGTGAGTTAT-3' (SEQ ID NO: 7) and a short oligonucleotide sequence: 5'-CG ATAACT CACCA/3Amino/-3' (SEQ ID NO: 8); sequences in the fourth row on the left are as follows: a long oligonucleotide sequence: 5'-AAGTAGGTATCmCmGTGAGTGGTGTAATGT-3' (SEQ ID NO: 9) and a short oligonucleotide sequence: 5'-CG ACATTA CACCA/3Amino/-3' (SEQ ID NO: 10); "3Amino" indicates that the 3' end of the oligonucleotide is modified by amino; and "Cm" represents C modified by methylation.

Further description of some accompanying drawings:

Description of FIG. 6:

The barcode-containing adapter is obtained through a treatment of two short single-stranded sequences by a special method, and a specific method is shown in step (6) of the above embodiment. The short adapter is not easy to break and may well bind to a DNA fragment. Wherein:

(1) Two Cm (double-underlined) in a long oligonucleotide represent C modified by methylation, which is intended to avoid conversion of C into U during methylation conversion.

(2) The 3' end of a short oligonucleotide is modified by amino (single-underlined and bold characters: 3'Amino), and the amino modification may prevent the ligation or polymerase linkage; and the 5' end has 5'-CG-3', which may be complementarily paired with a cohesive terminus-containing DNA fragment obtained after MspI cleavage (single-underlined), thereby making the adapter located to an end of the DNA fragment. It should be emphasized that a C base in 5'-CG-3' at the 5' end of the oligonucleotide does not have a phosphate group, or has other modifications, which ensures that the C base in the 5'-CG-3' at the 5' end cannot be ligated to the 3' end with hydroxyl of any DNA (including, but not limited to, fragmented DNA obtained after MspI cleavage, or other single-stranded oligonucleotides or double-stranded oligonucleotides) in a form of a phosphodiester bond.

(3) 6 pairs of complementarily-paired bases in a box constitute a barcode sequence with a tagging function, and theoretically, there are $4^6$ types of barcodes. In fact, a barcode may also be composed of 8, or 10 pairs of bases. Therefore, there are far more than $4^6$ types of barcodes, and there may be $4^8$, $4^{10}$, or more types of barcodes.

(4) 5 bases in brackets are used in combination with a J10P4 primer (AAGTAGGTATCCGTGAGTGGTG, SEQ ID NO: 3) used in the first round of PCR amplification for DNA fragment amplification.

Figure 7:
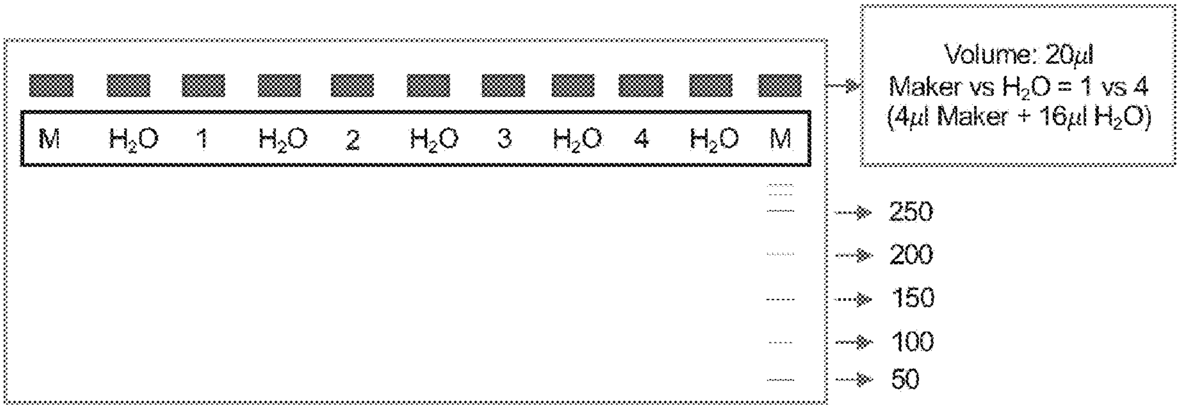
FIG. 7 is a spotting pattern in the method of the present application.

Description of FIG. 7:

(1) During spotting, Nuclease-Free Water should be used to separate maker and a sample and separate two samples, which avoids their mutual contamination.

(2) Only when a 50 bp fragment of a Maker band runs close to a bottom of a gel, the running of gels ends, such that DNA fragments may fully run, which is conducive to the recovery of fragments.

Finally, it should be noted that the above embodiments are provided merely to illustrate a technical solution of the present application, and are not intended to completely limit a protection scope of the present application. Although the present application is described in detail with reference to the preferred embodiments, those of ordinary skill in the art should understand that, even if the technical solution of the present application is modified or replaced in some aspects, a resulting technical solution does not depart from the essence and scope of the technology protected by the present application.

The invention claimed is:

1. A method for simultaneously detecting the methylation of CpG in a plurality of samples, comprising the following steps:

(I) independently lysing the plurality of samples to release respective genomic DNAs (gDNAs);

(II) purifying the released gDNAs or proceeding directly to the next step without purifying the released gDNAs;

(III) fragmenting the released gDNAs or purified gDNAs to obtain DNA fragments of different lengths, wherein the gDNAs are cleaved with a restriction endonuclease to allow DNA fragmentation, the restriction endonuclease is not sensitive to methylation, and 50% or more of bases of a recognition sequence for the restriction endonuclease are composed of C and G;

(IV) ligating DNA fragments of each of the samples to a barcode adapter with a different barcode, respectively;

(V) pooling DNA fragments of the plurality of the samples that are ligated with the barcode adapter to obtain a DNA fragment pool;

(VI) subjecting the pool of DNA fragments to repair of barcode adapters with a DNA polymerase to construct complete barcode adapters;

(VII) converting DNA fragments with the complete barcoded adapters, the conversion involving transformation of non-methylated deoxycytidine triphosphate (dCTP) into uridine triphosphate (UTP);

(VIII) subjecting converted DNA fragments to a first round of polymerase chain reaction (PCR) amplification, the amplification being conducted using primers compatible with barcode adapters and a DNA synthetase compatible with UTP, and the DNA synthetase guiding pairing of deoxyadenosine triphosphate (dATP) with UTP;

(IX) removing a primer sequence at the end of DNA fragments after the first round of PCR amplification according to the restriction endonuclease-associated sequence for primer excision and employing a corresponding restriction endonuclease, retaining a sample barcode sequence in the DNA fragment, and recovering DNA fragments;

(X) ligating the DNA fragments recovered in step (IX) to adapters with primers for a second round of PCR amplification, sequences of the adapters with primers for a second round of PCR amplification being compatible with a specific next-generation and/or third-generation high-throughput sequencing (HTS) platform;

(XI) subjecting the ligation product of step (X) to selection of fragment lengths, enrichment or recovery, and purification to obtain a preliminary sequencing library with sizes fitting the sequencing platform;

(XII) subjecting the ligation product obtained in step (XI) to the second round of PCR amplification, wherein the 3' end of a primer comprises an index for an experimental batch, and a primer pair used for the amplification is compatible with the specific next-generation or third-generation sequencing platform;

(XIII) subjecting an amplification product of step (XII) to selection of fragment lengths, enrichment or recovery, and purification to obtain a final sequencing library with sizes suitable for the sequencing platform;

(XIV) sequencing the final sequencing library obtained in step (XIII) with the specific next-generation or third-generation sequencing platform to obtain methylation data for the pooled plurality of samples; and (XV) decoding the methylation data obtained in step (XIV) through information analysis to obtain methylation patterns of each batch and each sample, wherein a sequence of one of the primers (J10P4) used for the first round of PCR amplification in step (VIII) is 5'AAGTAGGTATCCGTGAGTGGTG (SEQ ID NO: 3).

2. The method according to claim 1, wherein the restriction endonuclease in step (III) is a Type II restriction endonuclease capable of producing a cohesive terminus rather than a blunt terminus; and an enzyme cleavage is conducted through an independent action of one restriction endonuclease or a combined action of two or more restriction endonucleases.

3. The method according to claim 1, wherein the barcode adapter in step (IV) comprises a short oligonucleotide and a long oligonucleotide; the long oligonucleotide comprises a partial primer sequence for the first round of PCR amplification, a Type IIs restriction endonuclease recognition sequence required for primer removal, a cohesive terminus-associated sequence of a preset adapter, and a sample barcode sequence, sequentially from 5'-end to 3'-end; and the short oligonucleotide comprises a cohesive terminal sequence and a complementary sequence of the sample barcode sequence sequentially from 5'-end to 3'-end.

4. The method according to claim 3, wherein a Tm value of the short oligonucleotide is higher than 10° C. and lower than 60° C.; and the 5' end of the short oligonucleotide is blocked through preset modification avoiding forming a phosphodiester bond with 3' end hydroxyl (3'-hydroxyl) of any DNA fragment, and the 5' modification is lack of a 5'-phosphate group (free of 5'-phosphate).

5. The method according to claim 3, wherein the short oligonucleotide and the long oligonucleotide are denatured and then annealed to produce a long-short double-stranded DNA adapter; and the end of the long-short double-stranded DNA adapter corresponding to the 3' end of the long oligonucleotide is cohesive and is complementary to a cohesive terminus of CpG-enriched fragmented DNA.

6. The method according to claim 3, wherein a protruding sequence of a cohesive terminal of the short oligonucleotide is 5'CG; and the 5'CG is correspondingly paired with a cohesive terminus produced after cleavage of DNA by a restriction endonuclease MspI, and is unable to form a phosphodiester bond with a cohesive terminus produced after cleavage of DNA by MspI or a cohesive terminus of another double-stranded DNA adapter due to lack of a 5'-phosphate group in 5'C of the 5'CG.

7. The method according to claim 3, wherein the 3' end of the short oligonucleotide is modified by a group with a function of preventing ligation or polymerase extension; and the group modification is 3' dideoxycytidine (3'ddC), 3' inverted dT, 3' C3 spacer, 3' amino, or 3' phosphorylation.

8. The method according to claim 3, wherein a base of a deoxynucleotide at each position of the short oligonucleotide or the long oligonucleotide is any one selected from the group consisting of A, T, C, and G, or any one selected from the group consisting of 3 bases of A, T, C, and G, or any one selected from the group consisting of 2 bases of A, T, C, and G, or a specific base.

9. The method according to claim 3, wherein a base cytosine in the long oligonucleotide is methylated cytosine (named 5mC).

10. The method according to claim 3, wherein a number of bases of the sample barcode sequence is 2 to 10.

11. The method according to claim 3, wherein the Type IIs restriction endonuclease is BciVI.

12. The method according to claim 3, wherein there is a modification for stabilizing nucleotides and preventing the nucleotides from degradation by a nuclease between any two adjacent nucleotides in each of the barcode adapters, and the modification is a phosphorothioate modification.

13. The method according to claim 3, wherein a sequence of the long oligonucleotide is 5'AAG TAG GTA TCmCm GTG AGT GGTG AAGAAT (SEQ ID NO: 1).

14. The method according to claim 3, wherein a sequence of the short oligonucleotide is 5'CG ATTCTT CACCA/3Amino/(SEQ ID NO: 2).

15. The method according to claim 1, wherein the samples are single cells, a small number (micro-bulk) of cells, or extracted and purified DNA.

16. The method according to claim 1, wherein the repair of barcode adapters in step (VI) is conducted with a template-dependent DNA polymerase, and the template-dependent DNA polymerase has no activity of strand-displacement and no nicking activity.

17. The method according to claim 16, wherein the template-dependent DNA polymerase is *Sulfolobus* DNA Polymerase IV.

18. The method according to claim 16, wherein nucleotides used for the repair of barcode adapters in step (VI) are four mononucleotides: deoxyguanosine triphosphate (dGTP), deoxyadenosine triphosphate (dATP), deoxythymidine triphosphate (dTTP), and 5mdCTP, wherein the 5mdCTP is CTP modified by methylation (5mC for short).

19. The method according to claim 1, wherein the DNA fragment recovered in step (IX) has a length of 175 bp to 800 bp; and 2 size ranges of DNA fragments with lengths of 175 bp to 350 bp and 350 bp to 550 bp respectively are recovered separately and then sequenced, and the sequencing data of 2 size ranges of DNA fragments are merged.

* * * * *